United States Patent [19]
Dorner et al.

[11] Patent Number: 6,143,932
[45] Date of Patent: *Nov. 7, 2000

[54] SELECTIVELY N-ALKYLATED PEPTIDOMIMETIC COMBINATORIAL LIBRARIES AND COMPOUNDS THEREIN

[75] Inventors: Barbara Dorner, Basel, Switzerland; John M. Ostresh, Encinitas, Calif.; Colette T. Dooley, San Diego, Calif.; Richard A. Houghten, Del Mar, Calif.; Jutta Eichler, Cardiff, Calif.

[73] Assignee: Trega Biosciences, Inc., San Diego, Calif.

[*] Notice: This patent is subject to a terminal disclaimer.

[21] Appl. No.: 09/346,005

[22] Filed: Jul. 1, 1999

Related U.S. Application Data

[63] Continuation of application No. 08/811,830, Mar. 5, 1997
[60] Provisional application No. 60/046,871, Mar. 5, 1996.

[51] Int. Cl.$^7$ .................................................. C07C 233/05
[52] U.S. Cl. ......................... 564/153; 548/503; 548/507; 560/38; 560/169; 564/157; 564/230; 564/237; 564/240
[58] Field of Search .................................... 564/153, 157, 564/230, 237, 240, 337; 560/38, 169; 548/503, 507

[56] References Cited

U.S. PATENT DOCUMENTS

| | | |
|---|---|---|
| 4,278,793 | 7/1981 | Dürckheimer et al. . |
| 5,010,175 | 4/1991 | Rutter et al. . |
| 5,143,853 | 9/1992 | Walt . |
| 5,182,366 | 1/1993 | Huebner et al. . |
| 5,367,053 | 11/1994 | Dooley et al. . |
| 5,462,970 | 10/1995 | Bergeron et al. ........................ 514/654 |
| 5,719,193 | 2/1998 | Bowlin et al. ........................... 514/673 |

FOREIGN PATENT DOCUMENTS

| | | |
|---|---|---|
| 0 138 855 B1 | 3/1984 | European Pat. Off. . |
| WO 91/08694 | 6/1991 | WIPO . |
| WO 91/19735 | 12/1991 | WIPO . |
| WO 92/09300 | 6/1992 | WIPO . |

OTHER PUBLICATIONS

Dörner et al., "Generation of Peralkylated Peptidomimetic Combinatorial Libraries," *Methods in Molecular and Cellular Biology*, 6:17–22 (1996).
Ostresh et al., "Libraries from Libraries: Chemical Transformation of Combinatorial Libraries to Extend the Range and Repertoire of Chemical Diversity," *Proc. Natl. Acad. Sci. USA*, 91(23):11138–11142 (1994).
Houghten et al., "Libraries from Libraries: The Generation of Peptidomimetic Combinatorial Diversities," *Proc. Eur. Pept. Symp. 23*, pp. 459–460 (1994).
Bischoff, H., "Pharmacology of α-glucosidase inhibition," *Eur. J. Clin. Investig.*, 24(3):3–10 (1994).
Borch et al., "The Cyanohydridoborate Anion as a Selective Reducing Agent," *J. Am. Chem. Soc.*, 93:2897–2904 (1971).
Bradford, "A Rapid and Sensitive Method for the Quantitation of Microgram Quantities of Protein Utilizing the Principle of Protein–Dye Binding," *Anal. Biochem.*, 72:248–254 (1976).
Challis et al., "Reactions of the Carboxamide Group," *The Chemistry of Amides*, Zabicky, J. Ed.; Interscience: New York, pp. 731–857 (1970).
Coy et al., "Solid Phase Reductive Alkylation Techniques in Analogue Peptide Bond and Side–Chain Modification," *Tetrahedron*, 44:535–841 (1988).
Dooley et al., "An All D–Amino Acid Opioid Peptide with Central Analgesic Activity from a Combinatorial Library," *Science*, 266:2019–2022 (1994).
Dooley et al., "Identification of Mu–Selective Polyamine Antagonists from a Synthetic Combinatorial Library," *Analgesia*, 1:400–404 (1995).
Elbein, A.D., "Inhibitors of the Biosynthesis and Processing of N–Linked Oligosaccharide Chains," *Ann. Rev. Biochem.*, 56:497–534 (1987).
Fischer et al., The α–Glucosidase Inhibitor N–Butyldeoxynojirimycin Inhibits Human Immunodeficiency Virus Entry at the Level of Post–CD4 Binding, *J. Virol.*, 69(9) : 5791–5797 (1995).
Furka et al., "General method for rapid synthesis of multi component peptide mixtures," *Int. J. Pept. Protein Res.*, 37:487–493 (1991).
Gisin et al., "Carboxyl–Catalyzed Intramolecular Aminolysis. A Side Reaction in Solid–Phase Peptide Synthesis," *J. Am. Chem. Soc.*, 94:3102–3106 (1972).
Hakomori, S.–I., "A Rapid Permethylation of Glycolopid and Polysaccharide Catalyzed by Methylsulfinyl Carbanion in Dimethyl sulfoxide," *J. Biochem*, 55:205–208 (1964).
Haslvorson and Ellias, "The Purification and Properties of an α–Glucosidase of *Saccharomyces Italicus* Y1225," *Biochem. Biophys. Acta*, 30:28–40 (1958).
Houghten et al., "Simplified procedure for carrying out simultaneous multiple hydrogen fluoride cleavages of protected peptide resins," *Int. J. Pept. Protein Res.*, 27:673–678 (1986).
Houghten, R.A., "General method for the rapid solid–phase synthesis of large numbers of peptides: Specificity of antigen–antibody interaction at the level of individual amino acids," *Proc. Natl. Acad. Sci. USA*, 82:5131–5135 (1985).

(List continued on next page.)

Primary Examiner—Shailendra Kumar
Attorney, Agent, or Firm—Campbell & Flores LLP

[57] ABSTRACT

The instant invention is directed to a single, selectively N-alkylated compound and libraries of such compounds as set forth in Formula I. Furthermore, the instant invention is directed to methods of effecting analgesia, a decrease in the postprandial rise in the blood glucose levels of a mammal after ingestion of a carbohydrate load by said mammal, and treating microbial infections, utilizing such a single compound of Formula I in conjunction with a pharmaceutically-acceptable carrier. Also, the instant invention is directed to methods for selective alkylation, positional scanning and iterative synthetic and screening technologies.

30 Claims, No Drawings

OTHER PUBLICATIONS

Houghten et al., "Generation and use of systhetic peptide combinatorial libraries for basic research and drug discovery," *Nature*, 354:84–86 (1991).

Kaiser et al., "Color Test for Detection of Free Terminal Amino Groups in the Solid–Phase Synthesis of Peptides," *Anal Biochem*, 34:595 (1970).

Kajimoto et al., "Enyzme–Catalyzed Aldol Condensation for Asymmetric Synthesis of Azasugars: Synthesis, Evaluation, and Modeling of Glycosidase Inhibitors," *J. Am. Chem. Soc.*, 113:6187–6196 (1990).

Kornreich et al., "Peptide N–alkylamides by solid phase synthesis," *Int. J. Pept. Protein Res.*, 25:414–420 (1985).

Krchnak et al., "Noninvasive Continuous Monitoring or Solid–Phase Peptide Synthesis by Acid–Base Indicator," *Coll. Czech. Chem. Comm.*, 53:2542–2548 (1988).

Lam et al., "A new type of synthetic peptide library for identifying ligand–binding activity," *Nature*, 354:82–84 (1991).

Lebovitz, H.E., "Oral Antidiabetic Agents: The Emergence of α–Glucosidase Inhibitors," *Drugs*, 44(3) :21–28 (1992).

Merrifield, R.B., "Solid Phawse Peptide Synthesis. I. The Synthesis of a Tetrapeptide," *J. Am. Chem. Soc.*, 85:2149–2154 (1963).

Ostresh et al., "'Libraries from libraries': Chemical transformation of combinatorial libraries to extend the range and repertoire of chemical diversity," *Proc. Natl. Acad. Sci. USA*, 91:11138–11142 (1994).

Ostresh, J.M., et al., *Peptides 94: Proceedings of the 23rd European Peptide Symposium*, Maia, H.L.S. Ed.; Escom: Leiden, pp. 416–417 and 463–464 (1995).

Pili et al., "The α–Glucosidase I Inhibitor Castanospermine Alters Endothelial Cell Glycosylation, Prevents Angiogenesis, and Inhibits Tumor Growth," *Cancer Res.*, 55:2920–2926 (1995).

Rademacher, T.W., In: Sandler, M. and Smith, J.H. (Eds.), *Design Enzymes as Drugs*, 2:333–343 (1994).

Raucher et al., "A convenient method for the selective reduction of amides to amines," *Tetrahedron Letter*, 21:4061–4064 (1980).

Stankova et al., "Application of One–Bead One–Structure Approach to Identification of Nonpeptidic Ligands," *Drug Development Research*, 33:146–156 (1994).

Vilkas et al., "N–Methylation de Peptidase Par La Methode De Hakomori Structure Du Mycoside Cbl," *Tetrahedron Letters*, 26:3089 (1968).

Wann et al., "Reduction of Carboxylic Acid Derivatives by HBH4 in Acididc Dimehtyl Sulfoxide," *J. Org. Chem.*, 46:2579–2581 (1981).

Wong et al., "Synthesis and Evaluation of Homoazasugars as Glycosidase Inhibitors," *J. Org. Chem.*, 60:1492–1501 (1995).

SELECTIVELY N-ALKYLATED PEPTIDOMIMETIC COMBINATORIAL LIBRARIES AND COMPOUNDS THEREIN

This application is a continuation of U.S. Ser. No. 08/811,830, filed Mar. 5, 1997, which is a continuation of Provisional Application No. 60/046,871 filed Mar. 5, 1996.

FIELD OF THE INVENTION

The present invention relates generally to novel, selectively N-alkylated compounds of Formula I below, as well as novel libraries composed of many such compounds, methods of synthesizing and screening the libraries, and methods of using the compounds.

BACKGROUND INFORMATION

The process of discovering new therapeutically active compounds for a given indication involves the screening of all compounds from available compound collections. From the compounds tested, one or more structure(s) is selected as a promising lead. A large number of related analogs are then synthesized in order to develop a structure-activity relationship and select one or more optimal compounds. With traditional one-at-a-time synthesis and biological testing of analogs, this optimization process is long and labor intensive. Adding significant numbers of new structures to the compound collections used in the initial screening step of the discovery and optimization process cannot be accomplished with traditional one-at-a-time synthesis methods, except over a time frame of months or even years. Faster methods are needed that allow for the preparation of up to thousands of related compounds in a matter of days or a few weeks. This need is particularly evident when it comes to synthesizing more complex compounds, such as the instant compounds composed of two or more monomers, each monomer possessing more than one variable substituent.

Solid-phase techniques for the synthesis of peptides have been extensively developed and combinatorial libraries of peptides have been generated with great success. During the past four years there has been substantial development of chemically synthesized combinatorial libraries (SCLs) made up of peptides. The preparation and use of synthetic peptide combinatorial libraries has been described, for example, by Dooley in U.S. Pat. No. 5,367,053, Huebner in U.S. Pat. No. 5,182,366, Appel et al. in WO PCT 92/09300, Geysen in published European Patent Application 0 138 855 and Pirrung in U.S. Pat. No. 5,143,853. Such SCLs provide the efficient synthesis of an extraordinary number of various peptides in such libraries and the rapid screening of the library which identifies lead pharmaceutical peptides.

Substituent limitations have been overcome for mixtures of peptides and peptidomimetics through the use of solid phase techniques instead of the more traditional solution-phase ones. An important step in the development of solid-phase techniques was the discovery of methods to identify active individual compounds from soluble mixtures of large numbers of compounds, as described, for example by Rutter in U.S. Pat. No. 5,010,175 and Simon in WO PCT 91/19735. These soluble mixtures, however, have never before been applied to compounds with amide backbones that have different substituent on each amide nitrogen. Until now, it was possible by previously known methods to add only the same specific substituent to each and every nitrogen atom of the amide backbone. Thus, improved methods were needed to synthesize such selectively N-alkylated amide compounds.

This invention satisfies these needs and provides related advantages as well. The present invention overcomes the known limitations to the shortcomings of combinatorial chemistry with respect to selective N-alkylation. The present invention combines the techniques of solid-phase synthesis of peptidomimetic compounds and the general techniques of synthesis of combinatorial libraries to prepare new selective N-alkylated compounds.

SUMMARY OF THE INVENTION

This invention is directed to a single selectively N-alkylated compound or a library of an approximately equimolar mixture of two more selectively N-alkylated compounds of the Formula (I):

(I)

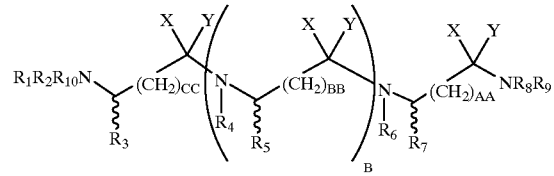

Wherein:

$R_1$ and $R_2$ independently are a hydrogen atom, an amino protecting group, $C_1$ to $C_{12}$ acyl, $C_3$ to $C_{10}$ cycloalkyl, $C_3$ to $C_6$ heterocycle, $C_1$ to $C_{12}$ alkyl, $C_1$ to $C_{12}$ substituted alkyl, $C_7$ to $C_{16}$ alkylaryl, $C_7$ to $C_{16}$ substituted alkylaryl, a $C_6$ to $C_{15}$ alkyl heterocycle, or a substituted $C_6$ to $C_{15}$ alkyl heterocycle;

$R_3$, $R_5$, and $R_7$ are independently a hydrogen atom, $C_1$ to $C_{12}$ alkyl, $C_1$ to $C_{12}$ substituted alkyl, phenyl, substituted phenyl, $C_7$ to $C_{16}$ alkylaryl, $C_7$ to $C_{16}$ substituted alkylaryl, a $C_6$ to $C_{15}$ alkyl heterocycle, or a substituted $C_6$ to $C_{15}$ alkyl heterocycle;

$R_4$, $R_6$, and $R_8$ are independently a $C_1$ to $C_{18}$ substituent group; with the proviso that all but one of $R_4$, $R_6$ and $R_8$ can simultaneously be the same group;

$R_9$ is a hydrogen atom or a solid support;

$R_{10}$ is optionally present as a $C_1$ to $C_{18}$ substituent group when $R_1$ and $R_2$ are other than a hydrogen atom, an amino protecting group or when both $R_1$ and $R_2$ are $C_1$ to $C_{12}$ acyl groups;

AA, BB, and CC are independently 0 to 5;

B is from 0 to 3;

further wherein the stereochemistry at the carbons bonded to $R_3$, $R_5$, and $R_7$ are independently R or S or a mixture of the two;

further wherein when B is 2 or 3; each $R_4$ and $R_5$ can be the same or different;

with the proviso that either $R_1$ or $R_2$ can be taken with $R_3$; $R_4$ can be taken with $R_5$; and $R_6$ can be taken with $R_7$; respectively and independently, to form a subtituted or unsubstituted pyrrolidine ring;

X and Y are either 1) each a hydrogen atom or 2) taken together to represent a carbonyl group;

and a pharmaceutically acceptable salt, solvate or hydrate thereof.

This invention is also directed to iterative and positional scanning methods of synthesizing the libraries of compounds described above as discussed below. Another aspect of the invention is a method of selective N-alkylation as set forth below. Furthermore, the invention comprises methods for affecting analgesia in a mammal, effecting a decrease in the postprandial rise in the blood glucose levels of a mammal after said mammal has ingested a carbohydrate load, and a method for treating microbial infections, all of which methods comprise administering a single compound of the above formula in conjunction with a pharmaceutically acceptable carrier, as set forth below.

DETAILED DESCRIPTION OF INVENTION

The instant invention is directed to a single compound or an approximately equimolar mixture of two or more selectively N-alkylated compounds of the Formula (I):

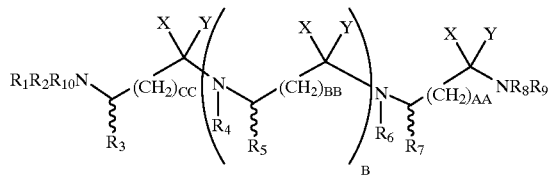

Wherein:

$R_1$ and $R_2$ independently are a hydrogen atom, an amino protecting group, $C_1$ to $C_{12}$ acyl, $C_3$ to $C_{10}$ cycloalkyl, $C_3$ to $C_6$ heterocycle, $C_1$ to $C_{12}$ alkyl, $C_1$ to $C_{12}$ substituted alkyl, $C_7$ to $C_{16}$ alkylaryl, $C_7$ to $C_{16}$ substitued alkylaryl, a $C_6$ to $C_{15}$ alkyl heterocycle, or a substituted $C_6$ to $C_{15}$ alkyl heterocycle;

$R_3$, $R_5$, and $R_7$ are independently a hydrogen atom, $C_1$ to $C_{12}$ alkyl, $C_1$ to $C_{12}$ substituted alkyl, phenyl, substituted phenyl, $C_7$ to $C_{16}$ alkylaryl, $C_7$ to $C_{16}$ substitued alkylaryl, a $C_6$ to $C_{15}$ alkyl heterocycle, or a substituted $C_6$ to $C_{15}$ alkyl heterocycle;

$R_4$, $R_6$, and $R_8$ are independently a $C_1$ to $C_{18}$ substituent group; with the proviso that all but one of $R_4$, $R_6$ and $R_8$ can simultaneoulsy be the same group;

$R_9$ is a hydrogen atom or a solid support;

$R_{10}$ is optionally present as a $C_1$ to $C_{18}$ substituent group when $R_1$ and $R_2$ are other than a hydrogen atom or an amino protecting group;

AA, BB, and CC are independently 0 to 5;

B is from 0 to 3;

further wherein the stereochemistry at the carbons bonded to $R_3$, $R_5$, and $R_7$ are independently R or S or a mixture of the two;

further wherein when B is 2 or 3; each $R_4$ and $R_5$ can be the same or different;

with the proviso that either $R_1$ or $R_2$ can be taken with $R_3$; $R_4$ can be taken with $R_5$; and $R_6$ can be taken with $R_7$; respectively and independently, to form a subtituted or unsubstituted pyrrolidine ring;

X and Y are either 1) each a hydrogen atom or 2) taken together to represent a carbonyl group;

and a pharmaceutically acceptable salt, solvate or hydrate thereof.

The terms used in the above Formula I having the following meanings when used in conjunction with Formula I and when used in described subsequent Formulas:

$C_3$ to $C_{10}$ cycloalkyl—unsubstituted or substituted mono- or bicyclic saturated rings such as cyclopropyl, cyclobutyl, cyclopentyl, cyclohexyl, cycloheptyl, or adamantyl or rings wherein the substituents are one or more hydroxy, halo, amino, protected amino, carboxy, protected carboxy, amido, nitro, trifluoromethyl, phenyl, heterocyclic rings, $C_1$ to $C_7$ acyl, $C_1$ to $C_7$ alkoxy, or $C_1$ to $C_3$ alkyl groups;

$C_3$ to $C_6$ heterocycle—unsubstituted or substituted mono- or bicyclic rings containing 3 to 6 carbons and from one to three nitrogen, oxygen, sulfur atoms such as azetidine, pyrrolidine, pyrazolidine, piperidine, piperazine, perhydroazepine or tropane, oxazole, thiazole, pyrazole, thiophenyl and pyranyl rings wherein the substituents are one or more hydroxy, protected hydroxy, halo, amino, protected amino, monosubstituted amino, disubstituted amino, carboxy, protected carboxy, amido, nitro, trifluoromethyl, phenyl, or $C_1$ to $C_3$ alkyl groups;

$C_1$ to $C_{12}$ Alkyl—straight-chain or branched carbon chain optionally containing a $C_3$ to $C_7$ saturated or partially saturated ring, wherein the carbon chain may also optionally be partially unsaturated, such as methyl, ethyl, tert-butyl, iso-propyl, 6-(cyclohexyl)-n-hexyl, allyl, n-octyl, 3-(cyclopentyl)-n-pentyl, methylcyclopropyl, and the like;

The term $C_1$ to $C_{18}$ Substituent Group indicates a group of the formula

wherein W is chosen from the group consisting of a hydrogen atom, $C_1$ to $C_{12}$ alkyl, $C_3$ to $C_{10}$ cycloalkyl, $C_1$ to $C_{12}$ substituted alkyl, phenyl, substituted phenyl, $C_7$ to $C_{16}$ alkylaryl, $C_7$ to $C_{16}$ substituted alkylaryl, as those terms are defined herein;

The term "$C_1$ to $C_{12}$ substituted alkyl," denotes the above $C_1$ to $C_{12}$ alkyl groups that are substituted by one to three halogen, hydroxy, protected hydroxy, amino, protected amino, guanidino, $C_1$ to $C_7$ acyloxy, $C_1$ to $C_7$ acyl, nitro, carboxy, protected carboxy, carboxamide, carbonyl, carboxyl, cyano, methylsulfonylamino or $C_1$ to $C_4$ alkoxy groups. The substituted alkyl groups may be substituted once or twice with the same or with different substituents;

Examples of the above substituted alkyl groups include the cyanomethyl, nitromethyl, hydroxymethyl, trityloxymethyl, propionyloxymethyl, aminomethyl, carboxymethyl, allyloxycarbonylmethyl, allyloxycarbonylaminomethyl, carbamoylmethyl, methoxymethyl, ethoxymethyl, t-butoxymethyl, acetoxymethyl, chloromethyl, bromomethyl, iodomethyl, 6-hydroxyhexyl, 2,4-dichloro(n-butyl), 2-amino(iso-propyl), 2-carbamoylethyl and the like. A preferred group of examples within the above "$C_1$ to $C_6$ substituted alkyl" group includes the substituted methyl group, in other words, a methyl group substituted by the same substituents as the "$C_1$ to $C_6$ substituted alkyl" group. Examples of the substituted methyl group include groups such as protected hydroxymethyl, (e.g., tetrahydropyranyloxymethyl), acetoxymethyl, carbamoylmethyl, chloromethyl, bromomethyl and iodomethyl.

The term "substituted phenyl" specifies a phenyl group substituted with one or more, and preferably one or two, moieties chosen from the groups consisting of halogen, hydroxy, protected hydroxy, cyano, nitro, trifluoromethyl, $C_1$ to $C_6$ alkyl, $C_1$ to $C_7$ alkoxy, $C_1$ to $C_7$ acyl, $C_1$ to $C_7$ acyloxy, carboxy, protected carboxy, carboxymethyl, protected carboxymethyl, hydroxymethyl, protected hydroxymethyl, amino, protected amino, (monosubstituted) amino, protected (monosubstituted) amino, (disubstituted) amino, carboxamide, protected carboxamide, N-($C_1$ to $C_6$ alkyl)carboxamide, protected N-($C_1$ to $C_6$ alkyl) carboxamide, N,N-di($C_1$ to $C_6$ alkyl)carboxamide, trifluoromethyl, N-(($C_1$ to $C_6$ alkyl)sulfonyl)amino, N-(phenylsulfonyl)amino or phenyl, substituted or unsubstituted, such that, for example, a biphenyl or naphthyl group results.

Examples of the term "substituted phenyl" includes a mono- or di(halo)phenyl group such as 2, 3 or 4-chlorophenyl, 2,6-dichlorophenyl, 2,5-dichlorophenyl, 3,4-dichlorophenyl, 2, 3 or 4-bromophenyl, 3,4-dibromophenyl, 3-chloro-4-fluorophenyl, 2, 3 or 4-fluorophenyl and the like; a mono or di(hydroxy)phenyl group such as 2, 3 or 4-hydroxyphenyl, 2,4-dihydroxyphenyl, the protected-hydroxy derivatives thereof and the like; a nitrophenyl group such as 2, 3 or 4-nitrophenyl; a cyanophenyl group, for example, 2, 3 or 4-cyanophenyl; a mono- or di(alkyl)phenyl group such as 2, 3 or 4-methylphenyl, 2,4-dimethylphenyl, 2, 3 or 4-(isopropyl)phenyl, 2, 3 or 4-ethylphenyl, 2, 3 or 4-(n-propyl) phenyl and the like; a mono or di(alkoxy)phenyl group, for example, 2,6-dimethoxyphenyl, 2, 3 or 4-methoxyphenyl, 2, 3 or 4-ethoxyphenyl, 2, 3 or 4-(isopropoxy)phenyl, 2, 3 or 4-(t-butoxy)phenyl, 3-ethoxy-4-methoxyphenyl and the like; 2, 3 or 4-trifluoromethylphenyl; a mono- or dicarboxyphenyl or (protected carboxy)phenyl group such as 2, 3 or 4-carboxyphenyl or 2,4-di(protected carboxy)phenyl; a mono- or di(hydroxymethyl)phenyl or (protected hydroxymethyl)phenyl such as 2, 3, or 4-(protected hydroxymethyl)phenyl or 3,4-di(hydroxymethyl)phenyl; a mono- or di(aminomethyl)phenyl or (protected aminomethyl)phenyl such as 2, 3 or 4-(aminomethyl)phenyl or 2,4-(protected aminomethyl)phenyl; or a mono- or di(N-(methylsulfonylamino))phenyl such as 2, 3 or 4-(N-(methylsulfonylamino))phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy 4-chlorophenyl and the like.

The terms "halo" and "halogen" refer to the fluoro, chloro, bromo or iodo groups. There can be one or more halogen, which are the same or different. Preferred halogens are chloro and fluoro.

The term "$C_7$ to $C_{16}$ alkylaryl" denotes a $C_1$ to $C_6$ alkyl group substituted at any position by a phenyl or naphthyl ring. Examples of such a group include benzyl, 2-phenylethyl, 3-phenyl(n-propyl), 4-phenylhexyl, 3-phenyl (n-amyl), 3-phenyl(sec-butyl) and the like. Preferred $C_7$ to $C_{16}$ phenylalkyl groups are the benzyl phenylethyl napth-1-ylmethyl and napth-2-ylmethyl groups.

The term "$C_7$ to $C_{16}$ substituted alkylaryl" denotes a $C_7$ to $C_{16}$ alkylaryl group substituted on the $C_1$ to $C_6$ alkyl portion with one or more, and preferably one or two, groups chosen from halogen, hydroxy, protected hydroxy, oxo, protected oxo, amino, protected amino, (monosubstituted)amino, protected (monosubstituted)amino, (disubstituted)amino, guanidino, heterocyclic ring, substituted heterocyclic ring, $C_1$ to $C_7$ alkoxy, $C_1$ to $C_7$ acyl, $C_1$ to $C_7$ acyloxy, nitro, carboxy, protected carboxy, carbamoyl, carboxamide, protected carboxamide, N-($C_1$ to $C_6$ alkyl)carboxamide, protected N-$C_1$ to $C_6$ alkyl)carboxamide, N, N-($C_1$ to $C_6$ dialkyl)carboxamide, cyano, N-(($C_1$ to $C_6$ alkylsulfonyl) amino, thiol, $C_1$ to $C_4$ alkylthio, $C_1$ to $C_4$ alkylsulfonyl groups; and/or the phenyl group may be substituted with one or more, and preferably one or two, substituents chosen from halogen, hydroxy, protected hydroxy, cyano, nitro, $C_1$ to $C_6$ alkyl, $C_1$ to $C_7$ alkoxy, $C_1$ to $C_7$ acyl, $C_1$ to $C_7$ acyloxy, carboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N-($C_1$ to $C_6$ alkyl) carboxamide, protected N-($C_1$ to $C_6$ alkyl) carboxamide, N, N-di($C_1$ to $C_6$ alkyl)carboxamide, trifluoromethyl, N-(($C_1$ to $C_6$ alkyl)sulfonyl)amino, N-(phenylsulfonyl)amino or a phenyl group, substituted or unsubstituted, for a resulting biphenyl or naphthyl group. The substituted alkyl or phenyl groups may be substituted with one or more, and preferably one or two, substituents which can be the same or different.

Examples of the term "$C_7$ to $C_{16}$ substituted alkylaryl" include groups such as 2-phenyl-1-chloroethyl, 2-(4-methoxyphenyl)ethyl, 4-(2,6-dihydroxyphenyl)n-hexyl, 2-(5-cyano-3-methoxyphenyl)n-pentyl, 3-(2,6-dimethylphenyl)n-propyl, 4-chloro-3-aminobenzyl, 6-(4-methoxyphenyl)-3-carboxy(n-hexyl), 5-(4-aminomethylphenyl)-3-(aminomethyl)n-pentyl, 5-phenyl-3-oxo-n-pent-1-yl, (4-hydroxynapth-2-yl)methyl and the like.

The term "(monosubstituted)amino" refers to an amino group with one substituent chosen from the group consisting of phenyl, substituted phenyl, $C_1$ to $C_6$ alkyl, $C_1$ to $C_6$ substituted alkyl, $C_1$ to $C_7$ acyl, $C_2$ to $C_7$ alkenyl, $C_2$ to $C_7$ substituted alkenyl, $C_2$ to $C_7$ alkynyl, $C_7$ to $C_{16}$ alkylaryl, $C_7$ to $C_{16}$ substituted alkylaryl and heterocyclic ring. The (monosubstituted)amino can additionally have an amino-protecting group as encompassed by the term "protected (monosubstituted)amino."

The term "(disubstituted)amino" refers to amino groups with two substituents chosen from the group consisting of phenyl, substituted phenyl, $C_1$ to $C_6$ alkyl, $C_1$ to $C_6$ substituted alkyl, $C_1$ to $C_7$ acyl, $C_2$ to $C_7$ alkenyl, $C_2$ to $C_7$ alkynyl, $C_7$ to $C_{16}$ alkylaryl, $C_7$ to $C_{16}$ substituted alkylaryl and heterocyclic ring. The two substituents can be the same or different.

The term "pharmaceutically-acceptable salt" encompasses those salts that form with the carboxylate anions and includes salts formed with the organic and inorganic cations such as those chosen from the alkali and alkaline earth metals, (for example, lithium, sodium, potassium, magnesium, barium and calcium); ammonium; and the organic cations (for example, dibenzylammonium, benzylammonium, 2-hydroxyethylammonium, bis(2-hydroxyethyl)ammonium, phenylethylbenzylammonium, dibenzylethylenediammonium, and like cations). Other cations encompassed by the above term include the protonated form of procaine, quinine and N-methylglucosamine, and the protonated forms of basic amino acids such as glycine, ornithine, histidine, phenylglycine, lysine, and arginine, and acetic acid-like counter-ions such as acetate and trifluoroacetate. Furthermore, any zwitterionic form of the instant compounds formed by a carboxylic acid and an amino group is referred to by this term. A preferred cation for the carboxylate anion is the sodium cation. Furthermore, the term includes salts that form by standard acid-base reactions with basic groups (such as amino groups) and organic or inorganic acids. Such acids include hydrochloric, sulfuric, phosphoric, acetic, succinic, citric, lactic, maleic, fumaric, palmitic, cholic, pamoic, mucic, D-glutamic, D-camphoric, glutaric, phthalic, tartaric, lauric, stearic, salicyclic, methanesulfonic, benzenesulfonic, sorbic, picric, benzoic, cinnamic, and the like acids.

The compounds of Formula I may also exist as solvates and hydrates. Thus, these compounds may crystallize with, for example, waters of hydration, or one, a number of, or any fraction thereof of molecules of the mother liquor solvent. The solvates and hydrates of such compounds are included within the scope of this invention.

The term "carboxy-protecting group" as used herein refers to one of the ester derivatives of the carboxylic acid group commonly employed to block or protect the carboxylic acid group while reactions are carried out on other functional groups on the compound. Examples of such carboxylic acid protecting groups include t-butyl, 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxytrityl, 4,4',4"-trimethoxytrityl, 2-phenylpropyl, trimethylsilyl, t-butyldimethylsilyl, phenacyl, 2,2,2-trichloroethyl, β-(trimethylsilyl)ethyl, β-(di(n-butyl)methylsilyl)ethyl, p-toluenesulfonylethyl, 4-nitrobenzylsulfonylethyl, allyl, cinnamyl, 1-(trimethylsilylmethyl)-propenyl and like moieties. The species of carboxy-protecting group employed is not critical so long as the derivatized carboxylic acid is stable to the conditions of subsequent reaction(s) and can be removed at the appropriate point without disrupting the remainder of the molecule. Further examples of these groups are found in C. B. Reese and E. Haslam, "Protective Groups in organic Chemistry," J. G. W. McOmie, Ed., Plenum Press, New York, N.Y., 1973, Chapter 5, respectively, and T. W. Greene and P. G. M. Wuts, "Protective Groups in Organic Synthesis," 2nd ed., John Wiley and Sons, New York, N.Y., 1991, Chapter 5, each of which is incorporated herein by reference. A related term is "protected carboxy," which refers to a carboxy group substituted with one of the above carboxy-protecting groups.

The term "hydroxy-protecting group" refers to readily cleavable groups bonded to hydroxyl groups, such as the tetrahydropyranyl, 2-methoxyprop-2-yl, 1-ethoxyeth-1-yl, methoxymethyl, β-methoxyethoxymethyl, methylthiomethyl, t-butyl, t-amyl, trityl, 4-methoxytrityl, 4,4'-dimethoxytrityl, 4,4',4"-trimethoxytrityl, benzyl, allyl, trimethylsilyl, (t-butyl)dimethylsilyl, 2,2,2-trichloroethoxycarbonyl groups and the like.

Further examples of hydroxy-protecting groups are described by C. B. Reese and E. Haslam, "Protective Groups in Organic Chemistry," J. G. W. McOmie, Ed., Plenum Press, New York, N.Y., 1973, Chapters 3 and 4, respectively, and T. W. Greene and P. G. M. Wuts, "Protective Groups in Organic Synthesis," Second Edition, John Wiley and Sons, New York, N.Y., 1991, Chapters 2 and 3. A preferred hydroxy-protecting group is the tert-butyl group. The related term "protected hydroxy" denotes a hydroxy group bonded to one of the above hydroxy protecting groups.

The term "amino-protecting group" as used herein refers to substituents of the amino group commonly employed to block or protect the amino functionality while reacting other functional groups of the molecule. The term "protected (monosubstituted)amino" means there is an amino-protecting group on the monosubstituted amino nitrogen atom. In addition, the term "protected carboxamide" means there is an amino-protecting group on the carboxamide nitrogen.

Examples of such amino-protecting groups include the formyl ("For") group, the trityl group, the phthalimido group, the trichloroacetyl group, the trifluoro-acetyl group, the chloroacetyl, bromoacetyl, and iodoacetyl groups, urethane-type blocking groups, such as t-butoxycarbonyl ("Boc"), 2-(4-biphenylyl)propyl-2-oxycarbonyl ("Bpoc"), 2-phenylpropyl-2-oxycarbonyl ("Poc"), 2-(4-xenyl) isopropoxycarbonyl, 1,1-diphenylethyl-1-oxycarbonyl, 1,1-diphenylpropyl-1-oxycarbonyl, 2-(3,5-dimethoxyphenyl) propyl-2-oxycarbonyl ("Ddz"), 2-(p-toluyl)propyl-2-oxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl) ethoxycarbonyl, 2-(methylsulfonyl)ethoxycarbonyl, 2-(triphenylphosphino)ethoxycarbonyl, 9-fluorenylmethoxycarbonyl ("Fmoc"), 2-(trimethylsilyl) ethoxycarbonyl, allyloxycarbonyl, 1-(trimethylsilylmethyl) prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, isobornyloxycarbonyl, 1-piperidyloxycarbonyl, benzyloxycarbonyl ("Cbz"), 4-phenylbenzyloxycarbonyl, 2-methylbenzyloxy-carbonyl, α-2,4,5,-tetramethylbenzyloxycarbonyl ("Tmz"), 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 4-(decyloxy) benzyloxycarbonyl and the like; the benzoylmethylsulfonyl group, 2,2,5,7,8-pentamethylchroman-6-sulfonyl group ("PMC") dithiasuccinoyl ("Dts"), the 2-(nitro) phenylsulfenyl group ("Nps"), the diphenyl-phosphine oxide group and like amino-protecting groups. The species of amino-protecting group employed is not critical so long as the derivatized amino group is stable to the conditions of the subsequent reaction(s) and can be removed at the appropriate point without disrupting the remainder of the compounds. Preferred amino-protecting groups are Boc, Cbz and Fmoc. Further examples of amino-protecting groups embraced by the above term are well known in organic synthesis and the peptide art and are described by, for example, T. W. Greene and P. G. M. Wuts, "Protective Groups in Organic Synthesis," 2nd ed., John Wiley and Sons, New York, N.Y., 1991, Chapter 7, M. Bodanzsky, "Principles of Peptide Synthesis," 1st and 2nd revised ed., Springer-Verlag, New York, N.Y., 1984 and 1993, and J. M. Stewart and J. D. Young, "Solid Phase Peptide Synthesis," 2nd ed., Pierce Chemical Co., Rockford, Ill., 1984, E. Atherton and R. C. Shephard, "Solid Phase Peptide Synthesis—A Practical Approach" IRL Press, Oxford, England (1989), each of which is incorporated herein by reference. The related term "protected amino" defines an amino group substituted with an amino-protecting group discussed above.

The term "heterocycle" denotes optionally substituted five-membered or six-membered rings that have 1 to 4 heteroatoms, such as oxygen, sulfur and/or nitrogen, in particular nitrogen, either alone or in conjunction with sulfur or oxygen ring atoms. These five-membered or six-membered rings may be saturated, fully unsaturated or partially unsaturated, with fully saturated rings being preferred. An "amino-substituted heterocyclic ring" means any one of the above-described heterocyclic rings is substituted with at least one amino group. Preferred heterocyclic rings include morpholino, piperidinyl, piperazinyl, tetrahydrofurano, pyrrolo, and tetrahydrothiophenyl.

Furthermore, the above optionally substituted five-membered or six-membered rings can optionally be fused to an aromatic 5-membered or 6-membered ring system, such as a pyridine or a triazole system, and preferably to a benzene ring.

The following ring systems are examples of the heterocyclic (whether substituted or unsubstituted) radicals denoted by the term "heterocyclic ring":thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, thiazinyl, oxazinyl, triazinyl, thiadiazinyl, oxadiazinyl, dithiazinyl, dioxazinyl, oxathiazinyl, tetrazinyl, thiatriazinyl, oxatriazinyl, dithiadiazinyl, imidazolinyl, dihydropyrimidyl, tetrahydropyrimidyl, tetrazolo[1,5-b]pyridazinyl and purinyl, as well as benzo-fused derivatives, for example benzoxazolyl, benzthiazolyl, benzimidazolyl and indolyl.

Further specific examples of the above heterocyclic ring systems are 6-membered ring systems containing one to three nitrogen atoms. Such examples include pyridyl, such as pyrid-2-yl, pyrid-3-yl and pyrid-4-yl; pyrimidyl, preferably pyrimid-2-yl and pyrimid-4-yl; triazinyl, preferably 1,3,4-triazin-2-yl and 1,3,5-triazin-4-yl; pyridazinyl, in particular pyridazin-3-yl, and pyrazinyl. The pyridine N-oxides and pyridazine N-oxides, and the pyridyl, pyrimid-2-yl, pyrimid-4-yl, pyridazinyl and the 1,3,4-triazin-2-yl radicals, are a preferred group.

The substituents for the optionally substituted heterocyclic ring systems, and further examples of the 5- and 6-membered ring systems discussed above, are found in W. Durckheimer et al., U.S. Pat. No. 4,278,793, issued Jul. 14, 1981, columns 9 through 21 and columns 188 through 233, herein incorporated by reference. (In columns 33 through 188, examples of the term "heterocyclic ring" are included in the heterocyclic thiomethyl groups listed under heading "A".)

The term "$C_6$ to $C_{15}$ alkyl heterocycle" denotes a $C_1$ to $C_6$ alkyl group substituted at any position by a heterocycle ring (heterocycle) from as described above, said heterocycle containing up to 14 carbon atoms, as long as sum of the carbon atoms of the alkyl chain (up to 6) and the carbon atoms of the heterocycle do not exceed 15. Similarly, the term "substituted $C_6$ to $C_{15}$ alkyl heterocycle" refer to a $C_6$ to $C_{15}$ alkyl heterocycle group substituted on the alkyl portion with the same substituents as listed for the $C_7$ to $C_{16}$ substituted alkylaryl groups and on the heterocycle as defined above for substituted heterocyle.

The above single compound or library of an approximately equal molar mixture of two or more compounds has several preferred embodiments. Specifically, in the embodiment where a single compound is indicated, a preferred group of single compounds are the interior amido compounds, that is, wherein X and Y are taken together to form a carbonyl moiety. A preferred group of interior amido single compounds are the dimers, thus, wherein B, AA, BB and CC are zero, except that AA can be zero or one when $R_7$ is a hydrogen atom and that CC can be zero or one when $R_3$ is a hydrogen atom. In turn, a preferred group of interior is amido dimers are those that are cleaved from the solid support and are not quaternized, thus, wherein $R_9$ is a hydrogen atom and $R_{10}$ is absent. A preferred group of cleaved interior amido dimer single compounds are those wherein $R_3$ and $R_7$ are independently chosen from the group consitig of S- or R-methyl, S- or R-benzyl, a hydrogen atom, S- or R-(but-2-yl), S- or R-[4-(N-methylamino)-n-butyl],S- or R-[4-(N-ethylamino)-n-butyl], S- or R-[4-(N-allylamino)-n-butyl], S- or R-[4-(N-benzylamino)-n-butyl], S- or R-[4-(N-(napth-2-ylmethylamino)-n-butyl], S- or R-[4-(amino)-n-butyl], S- or R-[sec-butyl], S- or R-(methylsulfinyl)eth-1-yl, S- or R-acetamido, S- or R-(N, N-dimethyl)acetamido, S- or R-(N,N-diethyl)acetamido, S- or R-(N,N-diallyl)acetamido, S- or R-(N-allyl)acetamido, S- or R-(N,N-dibenzyl)acetamido, S- or R-(N-benzyl) acetamido, S- or R-(N,N-di(napth-2-ylmethyl))acetamido, S- or R-(N-(napth-2-ylmethyl))acetamido, S- or R-propionamido, S- or R-(N,N-dimethyl)propionamido, S- or R-(N,N-diethyl)propionamido, S- or R-(N,N-diallyl) propionamido, S- or R-(N,N-dibenzyl)propionamido, S- or R-(N,N-di(napth-2-ylmethyl)propionamido, S- or R-[3-(guanidino)-n-propyl], S- or R-[(N,N-diallyl)-3-guanidino-n-propyl], S- or R-[(N,N,N'-triallyl)-3-guanidino-n-propyl], S- or R-[(N,N,N'-trimethyl)-3-(guanidino)-n-propyl], S- or R-[(N,N,N'-triethyl)-3-(guanidino)-n-propyl], S- or R-hydroxymethyl, S- or R-[1-(hydroxy)ethyl], S-phenyl, S- or R-[3-(carboxy)-n-propyl], S- or R-[iso-propyl], S- or R-[(indol-3-yl)methyl], S- or R-[(N-(methyl)indol-3-yl) methyl],S- or R-[(N-(ethyl)indol-3-yl)methyl], S- or R-[(N-(allyl)indol-3-yl)methyl], S- or R-[(N-(benzyl)indol-3-yl) methyl], S- or R-[(N-(naphth-2-ylmethyl)indol-3-yl) methyl], S- or R-(4-(methoxy))benzyl, S- or R-(4-(ethoxy)) benzyl, S- or R-(4-(allyloxy))benzyl, S- or R-[4-hydroxybenzyl], S- or R-(n-butyl), S- or R-(n-propyl), S- or R-[(napth-2-yl)methyl], AA is zero or one when $R_7$ is a hydrogen atom, CC is zero or one when $R_3$ is hydrogen atom, S- or R-[cyclohexylmethyl], S- or R-thiomethyl, or when either $R_1$ or $R_2$ are taken together with $R_3$ to form an S- or R-pyrrolidine or S-[4-(hydroxy)pyrrolidine].

An especially preferred group of single compounds referred to as cleaved interior amido dimers, hereafter referred to as the "Type I" amido dimers, is wherein $R_6$ and $R_8$ are independently methyl, ethyl, allyl, benzyl, or napth-2-ylmethyl. A preferred group of "Type I" amido dimers are the "Type II" amido diners, thus, wherein either $R_1$ or $R_2$ are each a hydrogen atom, or one of $R_1$ or $R_2$ is a hydrogen atom and the other is taken together with $R_3$ to form an S-pyrrolidine ring. A preferred group of the Type II interior amido dimers is the N-terminal monomer as a proline residue, thus, wherein one of $R_1$ or $R_2$ is a hydrogen atom and the other is taken together with $R_3$ to form an S-pyrrolidine ring. A preferred group of N-terminal proline Type II interior amido dimers occurs when $R_6$ is napth-2-ylmethyl and $R_8$ is benzyl, and more so when $R_7$ is S- or R-methyl, a hydrogen atom, S- or R-[3-(guanidino)-n-propyl], S- or R-[4-(N-benzylamino)-n-butyl], S-[iso-propyl], S-[2-(methylsulfinyl)ethyl], S- or R-(n-propyl), S- or R-(hydroxymethyl), S- or R-[n-butyl], R-[(napth-2-yl) methyl], or S-phenyl, and especially so when the C-terminal residue is S- or R-alanine, thus, $R_7$ is a S- or R-methyl.

Another preferred group of Type II interior amido dimers has the N-terminal residue as a S-phenylalanine, and more so wherein $R_6$ is ethyl and $R_8$ is (napth-2-yl)methyl, and especially so when $R_7$ is S-methyl, S-(2-(methylsulfinyl) ethyl), a hydrogen atom, S-(4-(hydroxy)benzyl) or S-[(hydroxy)methyl]. Of a special note within this preferred group of compounds is the compound wherein $R_7$ is S-methyl.

Another preferred group of Type I interior amido dimers are wherein $R_1$ and $R_2$ are each a hydrogen atom and $R_3$ is R-[(N-(napth-2-ylmethyl)indol-3-yl)methyl]. Of note within this preferred group of Type I compounds are wherein $R_6$ is napth-2-ylmethyl and $R_8$ is benzyl, and especially so when $R_7$ is S- or R-[3-(guanidino)-n-propyl] or S- or R-[4-(benzylamino)-n-butyl].

Yet another preferred group of Type I interior amido dimers occurs wherein either $R_1$ or $R_2$ is a hydrogen atom or is taken in conjunction with $R_3$ to form a pyrrolidine ring, and the other is $C_1$ to $C_{12}$ acyl, $C_3$ to $C_{10}$ cycloalkyl, $C_3$ to $C_6$ heterocycle, $C_1$ to $C_{12}$ alkyl, $C_1$ to $C_{12}$ substituted alkyl, $C_7$ to $C_{16}$ alkylaryl, $C_7$ to $C_{16}$ substitued alkylaryl, a $C_6$ to $C_{15}$ alkyl heterocycle, or a substituted $C_6$ to $C_{15}$ alkyl heterocycle.

Another preferred group of compounds of the above Formula I wherein a single compound is indicated is the interior amine compounds, in other words, wherein X and Y are each a hydrogen atom. A preferred group of these interior amine compounds is dimers, wherein B, AA, BB and CC are zero, except that AA can be zero or one when $R_7$ is a hydrogen atom and that CC can be zero or one when $R_3$ is a hydrogen atom. In turn, a preferred group of interior amine dimers is those cleaved from the solid support, thus, wherein $R_9$ is a hydrogen atom and $R_{10}$ is absent. A preferred group of cleaved interior amine dimers is those wherein $R_6$ and $R_8$ are independently methyl, benzyl or 4-hydroxybenzyl. A preferred group of these preferred cleaved interior dimers are referred to hereafter as "Type I cleaved interior amine dimers", that is, wherein $R_3$ and $R_7$ are independently benzyl or 4-hydroxybenzyl. A preferred group of the Type I cleaved interior amine dimers are those wherein $R_8$ is benzyl, $R_7$ is 4-hydroxybenzyl, $R_6$ is methyl, and $R_3$ is 4-hydroxybenzyl. A more preferred group of these Type I compounds are wherein a)$R_1$ and $R_2$ are the same and are methyl or a hydrogen atom; b)either $R_1$ or $R_2$ is a hydrogen atom and the other is chosen from the group consisting of methyl, isopropyl, cyclopropylmethyl, 4-hydroxymethyl, N-methylpiperidin-4-yl, and 3-(N,N-dimethylamino)-2-methylprop-2-en-1-yl. Another preferred group of Type I cleaved interior amine dimers are wherein $R_8$ is methyl, $R_7$ is benzyl, $R_6$ is 4-hydroxybenzyl, and $R_3$ is 4-hydroxybenzyl, and especially so wherein $R_1$ and $R_2$ are the same and are either a hydrogen atom or methyl, or one of $R_1$ or $R_2$ is a hydrogen atom and the other is methyl.

Yet another preferred group of Type I cleaved interior amine dimers are wherein $R_8$ is methyl, $R_7$ is 4-hydroxymethyl, $R_6$ is benzyl, and $R_3$ is 4-hydroxybenzyl, and especially so wherein $R_1$ and $R_2$ are the same and are either a hydrogen atom or methyl, or one of $R_1$ or $R_2$ is a hydrogen atom and the other is methyl.

Another preferred class of compounds within the invention encompassed by Formula I is a library of an approximately equimolar mixture of two or more compounds. A preferred group of this library of compounds are the interior amido compounds, thus, wherein X and Y are taken together to form a carbonyl group, and especially the interior amido dimers, wherein B, AA, BB and CC are zero, except that AA can be zero or one when $R_7$ is a hydrogen atom and that CC can be zero or one when $R_3$ is a hydrogen atom.

A preferred group of library of interior amido dimers are the resin-bound interior amido dimers, wherein $R_9$ is a solid support and $R_{10}$ is absent. A preferred group of these resin bound dimers are wherein $R_3$ and $R_7$ are independently chosen from the group consisting of S- or R-methyl, S- or R-benzyl, a hydrogen atom, S- or R-(but-2-yl), S- or R-[4-(t-butoxycarbonylamino)-n-butyl], S- or R-[sec-butyl], S- or R-(methylsulfinyl)eth-1-yl, S- or R-[3-(guanidino)-n-propyl], S- or R-[(N-PMC)-3-(guanidino)-n-propyl], S- or R-(t-butyloxy)methyl, S- or R-[2-(t-butyloxy)ethy], S-phenyl, S- or R-[2-(t-butoxycarbonyl)ethy], S- or R-[iso-propyl], S- or R-[(N-(t-butoxycarbonyl)indol-3-yl)methyl], S- or R-[4-hydroxybenzyl], S- or R-[(4-(t-butyloxy)) benzyl], S- or R-(n-propyl), S- or R-(n-butyl), S- or R-[(napth-2-yl)methyl], S- or R-(2-carboxyethyl), S- or R-(cyclohexylmethyl), S-[(4-methoxybenzylthio)methyl], S- or R-[(4- methylbenzylthio)methyl], S- or R-thiomethyl, S- or R-[4-(N-methyl-N-(t-butoxycarbonyl)amino)-n-butyl], S- or R-[4-(N-ethyl(N-(t-butoxycarbonyl)amino)-n-butyl], S- or R-[4-(N-allyl(N-(t-butoxycarbonyl)amino)-n-butyl], S- or R-[4-(N-benzyl(N-(t-butoxycarbonyl)amino)-n-butyl], S- or R-[4-(N-(naphth-2-yl)(N-(t-butoxycarbonyl)amino)-n-butyl], S- or R-acetamido, S- or R-[2-(N,N-dimethylamino)ethyl], S- or R-(N, N-diethyl)acetamido, S- or R-(N,N-diallyl)acetamido, S- or R-(N-allyl)acetamido, S- or R-(N,N-dibenzyl)acetamido, S- or R-(N-benzyl)acetamido, S- or R-(N,N-di(napth-2-ylmethyl))acetamido, S- or R-(N-(napth-2-ylmethyl))acetamido, S- or R-propionamido, S- or R-(N,N-dimethyl)propionamido, S- or R-(N,N-diethyl)propionamido, S- or R-(N,N-diallyl) propionamido, S- or R-(N,N-dibenzyl)propionamido, S- or R-(N,N-di(napth-2-ylmethyl)propionamido, S- or R-[(N,N'-diallyl-N-PMC)-3-guanidino-n-propyl], S- or R-[(N,N',N''-trimethyl-N-PMC)-3-(guanidino)-n-propyl], S- or R-[(N,N', N''-triethyl-N-PMC)-3-(guanidino)-n-propyl], S- or R-[N, N',N'' triallyl-N-PMC-3-(guanidino)-n-propyl], S- or R-[(indol-3-yl)methyl], S- or R-[(N-(methyl)indol-3-yl) methyl], S- or R-[(N-(ethyl)indol-3-yl)methyl], S- or R-[(N-(allyl)indol-3-yl)methyl], S- or R-[(N-(benzyl)indol-3-yl) methyl], S- or R-[(N-(naphth-2-ylmethyl)indol-3-yl) methyl], S- or R-(4-(methoxy))benzyl, S- or R-(4-(allyloxy))benzyl, S- or R-(4-(ethoxy))benzyl, S- or R-(4-(benzoxy))benzyl, S- or R-(4-(naphth-2-ylmethoxy))benzyl, AA is one or zero when $R_7$ is a hydrogen atom, CC is one or zero when $R_3$ is a hydrogen atom, or when either $R_1$ or $R_2$ are taken together with $R_3$ to form an S- or R- pyrrolidine or S-[4-(hydroxy)pyrrolidine].

A more preferred group of the library of resin-bound interior amido dimers, referred to hereafter as the "Type I bound amido dimers (Library)", occurs wherein $R_6$ and $R_8$ are independently methyl, ethyl, allyl, benzyl, or napth-2-ylmethyl. A preferred group of the Type I bound amido dimers (Library) is wherein either $R_1$ or $R_2$ is a hydrogen atom or is taken in conjunction with $R_3$ to form a pyrrolidine ring, and the other is $C_1$ to $C_{12}$ acyl, $C_3$ to $C_{10}$ cycloalkyl, $C_3$ to $C_6$ heterocycle, $C_1$ to $C_{12}$alkyl, $C_1$ to $C_{12}$ substituted alkyl, $C_7$ to $C_{16}$ alkylaryl, $C_7$ to $C_{16}$ substitued alkylaryl, a $C_6$ to $C_{15}$ alkyl heterocycle, or a substituted $C_6$ to $C_{15}$ alkyl heterocycle.

Another preferred group of the Type I bound amido dimers (Library) is wherein either $R_1$ or $R_2$ are each a hydrogen atom, or one of $R_1$ or $R_2$ is a hydrogen atom and the other is taken together with $R_3$ to form an S-pyrrolidine ring.

Another preferred group of interior amido dimers (Library) are those that have been cleaved from the solid support, hereinafter referred to as "cleaved interior amido dimers (Library)", and in the above Formula I corresponds to wherein $R_9$ is hydrogen and $R_{10}$ is absent. A preferred group of cleaved interior amido dimers are wherein $R_3$ and $R_7$ are independently chosen from the group consisting of S- or R-methyl, S- or R-benzyl, a hydrogen atom, S- or R-(but-2-yl), S- or R-[4-(N-methylamino)-n-butyl], S- or R-[4-(N-ethylamino)-n-butyl], S- or R-[(4-(N-allylamino)-n-butyl], S- or R-[4-(N-benzylamino)-n-butyl], S- or R-[4-(N-(napth-2-ylmethylamino)-n-butyl], S- or R-[4-(amino)-n-butyl], S- or R-[sec-butyl], S- or R-(methylsulfinyl)eth-1-yl, S- or R-acetamido, S- or R-[2-(N,N-dimethyl) acetamido], S- or R-(N, N-diethyl)acetamido, S- or R-(N, N-diallyl)acetamido, S- or R-(N-allyl)acetamido, S- or R-(N,N-dibenzyl)acetamido, S- or R-(N-benzylacetamido, S- and R-(N,N-di(napth-2-ylmethyl)acetamido, S- and R-(N-(napth-2-ylmethyl)acetamido, S- or R-(N,N-dimethyl) propionamido, S- or R-(N,N-diethyl)propionamido, S- or R-(N,N-dially)propionamido, S- or R-(N,N-dibenzyl) propionamido, S- or R-(N,N-di(napth-2-ylmethyl) propionamido, S- or R-[3-(guanidino)-n-propyl], S- or R-[((N,N-diallyl)-3-guanidino-n-propyl], S- or R-[(N,N,N'-triallyl)-3-guanidino-n-propyl], S- or R-[(N,N,N'-trimethyl)-3-(guanidino)-n-propyl], S- or R-[(N,N,N'-triethyl)-3-(guanidino)-n-propyl], S- or R-hydroxymethyl, S- or R-[1-(hydroxy)ethyl], S-phenyl, S- or R-[2-(carboxy) ethyl], S- or R-[iso-propyl], S- or R-[(indol-3-yl)methyl], S- or R-[(N-(methyl)indol-3-yl)methyl], S- or R-[(N-(ethyl) indol-3-yl)methyl], S- or R-[(N-(allyl)indol-3-yl)methyl], S- or R-[(N-(benzyl)indol-3-yl)methyl], S- or R-[(N-(naphth-2-ylmethyl)indol-3-yl)methyl], S- or R-(4-(methoxy))benzyl, S- or R-(4-(ethoxy))benzyl, S- or R-(4-(allyloxy))benzyl, S- or R-[4-hydroxybenzyl], S- or R-(n-butyl), S- or R-(n-propyl), S- or R-[(napth-2-yl)methyl], AA is zero when $R_7$ is hydrogen, CC is zero or one when $R_3$ is a hydrogen atom, S- or R-(cyclohexylmethyl), S- or R-thiomethyl, or when either $R_1$ or $R_2$ are taken together with $R_3$ to form an S- or R-pyrrolidine or S-[4-(hydroxy)pyrrolidine].

A more preferred group of library of cleaved interior dimers, hereinafter referred to as "Type I cleaved amido dimers", wherein $R_6$ and $R_8$ are independently methyl, ethyl, allyl, benzyl, or napth-2-ylmethyl. Specific examples of the Type I cleaved amido dimers occur when:

(1) wherein $R_6$ is napth-2-ylmethyl, $R_3$ is R-[(N-(naphth-2-ylmethyl)indol-3-yl)methyl], and $R_1$ and $R_2$ are the same and are each a hydrogen atom;

(2) wherein $R_6$ is ethyl, $R_3$ is benzyl and $R_1$ and $R_2$ are the same and are each a hydrogen atom;

(3) wherein $R_6$ is naphth-2-ylmethyl, $R_3$ is S-methyl, $R_1$ and $R_2$ are the same and are each a hydrogen atom; and (4) wherein either $R_1$ or $R_2$ is a hydrogen atom and the other is taken in conjunction with $R_3$ to form an S-pyrrolidine ring, and $R_6$ is napth-2-ylmethyl.

Another preferred group of compounds within the library of an approximately equimolar mixture of two or more compounds of Formula I are the interior amine compounds, thus, wherein in the above Formula I, X and Y are the same and are each a hydrogen atom. A preferred library of interior amine compounds are those that are dimers, that is wherein B, AA, BB and CC are zero, except that AA can be zero or one when $R_7$ is a hydrogen atom and that CC can be zero or one when $R_3$ is a hydrogen atom. Preferred interior amine dimers (Library) are those that have been cleaved from the solid support, wherein $R_9$ is a hydrogen atom and $R_{10}$ is absent. A preferred group of such cleaved interior amine dimers are wherein $R_3$ and $R_7$ are independently chosen from the group consisting of S- or R-methyl, S- or R-benzyl, a hydrogen atom, S- or R-(but-2-yl), S- or R-[4-(N-methylamino)-n-butyl], S- or R[(4-(N-ethylamino)-n-butyl], S- or R-[4-(N-allylamino)-n-butyl], S- or R-[4-(N-benzylamino)-n-butyl], S- or R-[4-(N-(napth-2-ylmethylamino)-n-butyl], S- or R-[4-(amino)-n-butyl], S- or R-[sec-butyl], S- or R-(2-aminoethyl), S- or R-(methylsulfinyl)eth-1-yl, S- or R-[2-(N,N-dimethylamino)ethyl], S- or R-(N, N-diethylamino)ethyl, S- or R-(N,N-diallylamino)ethyl, S- or R-(N-allylamino)ethyl, S- or R-(N,N-dibenzylamino)ethyl, S- or R-(N-benzylamino)ethyl, S- and R-(N,N-di(napth-2-ylmethylamino))ethyl, S- and R-(N-(napth-2-ylmethylamino))ethyl, S- or R-(N-propyl)amine, S- or R-(N, N-dimethylamino)propyl, S- or R-(N,N-diethylamino)propyl, S- or R-(N,N-diallylamino)propyl, S- or R-(N,N-dibenzylamino)propyl, S- or R-(N,N-di(napth-2-ylmethylamino)propyl, S- or R-[3-(guanidino)-n-propyl], S- or R-[(N,N-diallyl)-3-guanidino-n-propyl], S- or R-[(N,N,N'-triallyl)-3-guanidino-n-propyl], S- or R-[(N,N,N'-trimethyl)-3-(guanidino)-n-propyl], S- or R-[(N,N,N'-triethyl)-3-(guanidino)-n-propyl], S- or R-hydroxymethyl, S- or R-[1-(hydroxy)ethyl], S-phenyl, S- or R-[3-(hydroxy)-n-propyl], S- or R-[iso-propyl], S- or R-[(indol-3-yl)methyl], S- or R-[(N-(methyl)indol-3-yl)methyl],S- or R-[(N-(ethyl)indol-3-yl)methyl], S- or R-[(N-(allyl)indol-3-yl)methyl], S- or R-[(N-(benzyl)indol-3-yl)methyl], S- or R-[(N-(naphth-2-ylmethyl)indol-3-yl)methyl], S- or R-(4-(methoxy))benzyl, S- or R-(4-(ethoxy))benzyl, S- or R-(4-(allyloxy))benzyl, S- or R-(4-hydroxybenzyl), S- or R-(n-butyl), S- or R-(n-propyl), S- or R-[(napth-2-yl)methyl], AA is zero or one when $R_7$ is a hydrogen atom, CC is zero or one when $R_3$ is a hydrogen atom, S- or R-(cyclohexylmethyl), S- or R-thiomethyl, or when either $R_1$ or $R_2$ are taken together with $R_3$ to form an S- or R-pyrrolidine or S-[4-(hydroxy)pyrrolidine]. A preferred group of dimers within the immediately preceeding preferred group occurs when $R_6$ and $R_8$ are independently methyl, ethyl, allyl, benzyl, or napth-2-ylmethyl.

Another preferred group within the library of interior amine dimers are the resin-bound compounds, thus, wherein $R_9$ is a solid support and $R_{10}$ is absent. A preferred group of the resin-bound interior amine dimers (Library) occurs wherein $R_3$ and $R_7$ are independently chosen from the group consisting of S- or R-methyl, S- or R-benzyl, a hydrogen atom, S- or R-(but-2-yl), S- or R-[4-(N-methylamino)-n-butyl], S- or R-[4-(N,N-dimethylamino)-n-butyl], S- or R-[4-(N-ethylamino)-n-butyl], S- or R-[4-(N-methyl-N-ethylamino)-n-butyl], S- or R-[4-(N-allylamino)-n-butyl], S- or R-[4-(N-methyl-N-alkylamino)-n-butyl], S- or R-[4-(N-benzylamino)-n-butyl], S- or R-[4-(N-methyl-N-benzylamino)-n-butyl], S- or R-[4-(N-(napth-2-ylmethylamino)-n-butyl], S- or R-[4-(N-methyl-N-naphth-2-ylmethylamino)-n-butyl], S- or R-[4-(amino)-n-butyl], S- or R-[sec-butyl], S- or R-(2-aminoethyl), S- or R-(methylsulfinyl)eth-1-yl, S- or R-acetamido, S- or R-[2-(N,N-dimethylamino)ethyl], S- or R-(N,N-diethylamino)ethyl, S- or R-(N,N-diallylamino)ethyl, S- or R-(n-allylamino)ethyl, S- or R-(N,N-dibenzylamino)ethyl, S- or R-(N-benzylamino)ethyl, S- or R-(N,N-di(napth-2-ylmethylamino))ethyl, S- or R-(N-(napth-2-ylmethylamino))ethyl, S- or R-(N-propylamine), S- or R-propionamido, S- or R-(N,N-dimethylamino)propyl, S- or R-(N,N-diethylamino)propyl, S- or R-(N,N-diallylamino)propyl, S- or R-(N,N-dibenzylamino)propyl, S- or R-(N,N-di(napth-2-ylmethylamino)propyl, S- or R-[3-(N-PMC-guanidino)-n-propyl], S- or R-[(N,N'-diallyl-N-PMC)-3-guanidino-n-propyl], S- or R-[(N,N',N"-triallyl-N-PMC)-3-guanidino-n-propyl], S- or R-[(N,N',N"-trimethyl-N-PMC)-3-(guanidino)-n-propyl], S- or R-[(N,N',N"-triethyl-N-PMC)-3-(guanidino)-n-propyl], S- or R-hydroxymethyl, S- or R-[1-(hydroxy)ethyl], S-phenyl, S- or R-[3-(hydroxy)-n-propyl], S- or R-[iso-propyl], S- or R-[(indol-3-yl)methyl], S- or R-[(N-(methyl)indol-3-yl)methyl],S- or R-[(N-(ethyl)indol-3-yl)methyl], S- or R-[(N-(allyl)indol-3-yl)methyl], S- or R-[(N-(benzyl)indol-3-yl)methyl], S- or R-[(N-(naphth-2-ylmethyl)indol-3-yl)methyl], S- or R-(4-(methoxy))benzyl, S- or R-(4-(ethoxy))benzyl, S- or R-(4-(allyloxy))benzyl, S- or R-[4-hydroxybenzyl], S- or R-[n-butyl], S- or R-(n-propyl), S- or R-[(napth-2-yl)methyl], AA is zero or one when $R_7$ is a hydrogen atom, CC is zero or one when $R_3$ is a hydrogen atom, S- or R-[cyclohexylmethyl], S- or R-[thiomethyl], or when either $R_1$ or $R_2$ are taken together with $R_3$ to form an S- or R-pyrrolidine or S-[4-(hydroxy)pyrrolidine]. A still more preferred group within the library of resin bound interior amine dimers occurs when $R_6$ and $R_8$ are independently methyl, ethyl, allyl, benzyl, or napth-2-ylmethyl.

Another aspect of the instant invention is a method for effecting analgesia in a mammal, which comprises administering an effective amount of a single compound of Formula I in conjunction with a pharmaceutically-acceptable carrier. A preferred method of effecting analgesia in a mammal occurs when a single compound that is an interior amido dimer and further wherein B, AA, BB and CC are zero, $R_9$ is a hydrogen atom, $R_8$ is napth-2-ylmethyl, $R_7$ is S-methyl, $R_6$ is ethyl, $R_3$ is S-benzyl, and $R_1$ and $R_2$ are each a hydrogen atom is used. Another preferred method of effecting analgesia in mammals utilizes a single interior amine dimer wherein further $R_9$ is a hydrogen atom, $R_8$ is benzyl, $R_7$ is S-methyl, $R_6$ is naphth-2-ylmethyl, $R_3$ is taken in conjunction with either $R_1$ or $R_2$ to form an S-pyrrolidine ring and the other of $R_1$ and $R_2$ a hydrogen atom.

Another aspect of the instant invention is a method of effecting a decrease in the postprandial rise in blood glucose of a mammal after ingestion of a carbohydrate load by said mammal, which comprises administering an effective amount of a single compound of Formula I in conjunction with a pharmaceutically-acceptable carrier. A preferred method of affecting a decrease in the postprandial rise in the blood glucose of a mammal occurs wherein the single compound has X and Y taken together to form a carbonyl group, B, AA, BB and CC are zero, $R_9$ is a hydrogen atom, $R_8$ is benzyl, $R_6$ is naphth-2-ylmethyl, $R_3$ is R-(N-(naphth-2-ylmethyl)indol-3-ylmethyl), $R_1$ and $R_2$ are each hydrogen, $R_{10}$ is absent, and $R_7$ is chosen from the group consisting of S-(4-(N-benzylamino)-n-butyl), R-(4-(N-benzylamino)-n-butyl), S-(3-guanidino)-n-propyl), and R-(3-guanidino)-n-propyl).

Yet another aspect of the instant invention is a method of treating microbial infections in mammals, which comprises administering an effective amount of a single compound of Formula I in conjunction with a pharmaceutically-acceptable carrier. A preferred method of treating microbial infections in mammals occurs when wherein the single compound has X and Y taken together to form a carbonyl group, B, AA, BB and CC are zero, $R_9$ is a hydrogen atom, $R_8$ is benzyl, $R_6$ is naphth-2-ylmethyl, $R_3$ is R-(N-(naphth-2-ylmethyl)indol-3-ylmethyl), $R_1$ and $R_2$ are each hydrogen, $R_{10}$ is absent, and $R_7$ is chosen from the group consisting of S-(4-(N-benzylamino)-n-butyl), R-(4-(N-benzylamino)-n-butyl), S-(3-guanidino)-n-propyl), and R-(3-guanidino)-n-propyl).

Another aspect of the instant invention is a method of step-wise N-alkylation of the amide bond of the N-terminal residue of a compound of the Formula (II):

$$\text{Trityl—N(H)—C(R}_{11}\text{)—(CH}_2\text{)}_{ZZ}\text{—C(O)—NH—R}_{12} \quad \text{(II)}$$

Wherein:

$R_{11}$ is independently a hydrogen atom, $C_1$ to $C_{12}$ alkyl, $C_1$ to $C_{12}$ substituted alkyl, phenyl, substituted phenyl, $C_7$ to $C_{16}$ alkylaryl, $C_7$ to $C_{16}$ substitued alkylaryl, a $C_6$ to $C_{15}$ alkyl heterocycleal, or a substituted $C_6$ to $C_{15}$ alkyl heterocycle;

ZZ is from zero to five;

And $R_{12}$ is a solid support or a group of the Formula (III):

$$\left( \text{C(R}_{13}\text{)—(CH}_2\text{)}_{YY}\text{—C(O)—NR}_{14}\text{R}_{15} \right)_W \quad \text{(III)}$$

Wherein $R_{14}$ is a $C_1$ to $C_{18}$ substituent group;
Wherein W is 0 to 4;
$R_{13}$ is independently a hydrogen atom, $C_1$ to $C_{12}$ alkyl, $C_1$ to $C_{12}$ substituted alkyl, phenyl, substituted phenyl, $C_7$ to $C_{16}$ alkylaryl, $C_7$ to $C_{16}$ substitued alkylaryl, a $C_6$ to $C_{15}$ alkyl heterocycle, or a substituted $C_6$ to $C_{15}$ alkyl heterocycle;

$R_{15}$ is a solid support (when W is one) or a bond to the preceeding methylene group (when W is from two to four);
YY is from zero to five;

Wherein the compound of the above formula is a)first reacted under anhydrous conditions in an inert atmosphere with an excess amount non-nucleophilic base having a pKa between about 18 to about 40; then b)reacting the resulting anion under anhydrous conditions in an inert atmosphere in a polar aprotic solvent with an excess amount of an alkylting agent of the formula (LG)-Q Wherein LG is leaving group;
Q is a $C_1$ to $C_{18}$ substituent groups as defined above for Formula (I);
and repeating steps a) and b) as necessary to drive the alkylation to completion;
with the proviso that all previous internal backbone amide bonds have been previously alkylated with a $C_1$ to $C_{18}$ substituent group and, when W is from 2 to 4, all of the $R_{14}$ groups are not the same $C_1$ to $C_{18}$ substituent group.

A preferred method of step-wise N-alkylation occurs when LG is iodo or bromo and the —CH$_2$-Q moiety is methyl, ethyl, allyl, benzyl or napth-2-ylmethyl. A further preferred method of step-wise N-alkylation occurs wherein $R_{11}$ and $R_{13}$ are indepently chosen from the group consisting of S- or R-methyl, S- or R-benzyl, a hydrogen atom, S- or R-(but-2-yl), S- or R-[4-(t-butoxycarbonylamino)-n-butyl], S- or R-[4-(amino)-n-butyl], S- or R-[sec-butyl], S- or R-(methylsulfinyl)eth-1-yl, S- or R-[3-(guanidino)-n-propyl], S- or R-[(N-PMC)-3-(guanidino)-n-propyl], S- or R-(t-butoxy)methyl, S- or R-[2-(t-butoxy)ethy], S-phenyl, S- or R-(3-(2-butoxycarbonyl)ethyl), S- or R-[iso-propyl], S- or R-[(N-(t-butoxycarbonyl)indol-3-yl)methyl], S- or R-[4-hydroxybenzyl], S- or R-[(4-(t-butoxy))benzyl], S- or R-[n-propyl], S- or R-(n-butyl), S- or R-[(napth-2-yl)methyl], S- or R-(cyclohexylmethyl), S-[(4-methoxybenzylthio)methyl], S-[(4-methylbenzylthio) methyl], S- or R-thiomethyl, S- or R-[4-(N-methyl-(N-(t-butoxycarbonyl))amino)-n-butyl], S- or R-[4-(N-ethyl-(N-(t-butoxycarbonyl))amino)-n-butyl], S- or R-[4-(N-allyl-(N-(t-butoxycarbonyl))amino)-n-butyl], S- or R-[4-(N-benzyl-(N-(t-butoxycarbonyl))amino)-n-butyl], S- or R-[4-(N-(naphth-2-yl)-(N-(t-butoxycarbonyl))amino)-n-butyl], S- or R-[2-(N,N-dimethyl)acetamido], S- or R-acetamido, S- or R-(N, N-diethyl)acetamido, S- or R-(N,N-diallyl)acetamido, S- or R-(n-allyl)acetamido, S- or R-(N,N-dibenzyl) acetamido, S- or R-(N-benzyl)acetamido, S- or R-(N,N-di (napth-2-ylmethyl))acetamido, S- or R-(N-(napth-2-ylmethyl))acetamido, S- or R-n-propylamine, S- or R-propionamido, S- or R-(N,N-dimethyl)propionamido, S- or R-(N,N-diethyl)propionamido, S- or R-(N,N-diallyl) propionamido, S- or R-(N,N-dibenzyl)propionamido, S- or R-(N,N-di(napth-2-ylmethyl)propionamido, S- or R-[(N,N'-diallyl-N-PMC)-3-guanidino-n-propyl], S- or R-[(N,N',N"-trimethyl-N-PMC)-3-(guanidino)-n-propyl], S- or R-[(N,N', N"-triethyl-N-PMC)-3-(guanidino)-n-propyl], S- or R-[N, N',N"-triallyl-N-PMC)-3-guanidino-n-propyl], S- or R-[(indol-3-yl)methyl], S- or R-[(N-(methyl)indol-3-yl) methyl], S- or R-[(N-(ethyl)indol-3-yl)methyl], S- or R-[(N-(allyl)indol-3-yl)methyl], S- or R-[(N-(benzyl)indol-3-yl) methyl], S- or R- [(N-(naphth-2-ylmethyl)indol-3-yl) methyl], S- or R-(4-(methoxy))benzyl, S- or R-(4-(ethoxy)) benzyl, S- or R-(4-(allyloxy))benzyl, S- or R-(4-(benzoxy) benzyl, S- or R-(4-(naphth-2-ylnethoxy)benzyl, ZZ is one or zero when $R_{11}$ is a hydrogen atom, YY is one or zero when $R_{13}$ is a hydrogen atom, or when either $R_{13}$ is taken together with $R_{14}$ to form an S- or R-pyrrolidine or S-[4-(hydroxy) pyrrolidine].

Another aspect of the instant invention utilizes the positional scanning method and is a method of synthesizing and testing for biological activity a library of an approximately equimolar amount of compounds of the following Formula (IV):

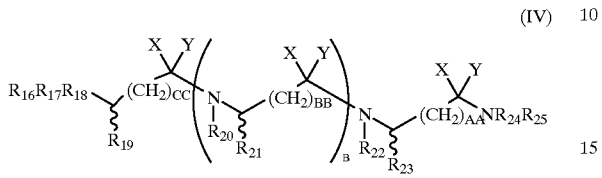

Wherein in the above Formula (IV):

$R_{19}$, $R_{21}$ and $R_{23}$ independently are a hydrogen atom, $C_1$ to $C_{12}$ alkyl, $C_1$ to $C_{12}$ substituted alkyl, phenyl, substituted phenyl, $C_7$ to $C_{16}$ alkylaryl, $C_7$ to $C_{16}$ substitued alkylaryl, a $C_6$ to $C_{15}$ alkyl heterocycle, or a substituted $C_6$ to $C_{15}$ alkyl heterocycle;

$R_{25}$ is a hydrogen atom or a solid support;

$R_{20}$, $R_{22}$ and $R_{24}$ are independently a $C_1$ to $C_{18}$ substituent group;

AA, BB and CC are independently 0 to 5;

B is from 0 to 3;

X and Y are taken together to form a carbonyl group or are separate and are each a hydrogen atom;

$R_{16}$, $R_{17}$ and $R_{18}$ independently are a hydrogen atom, an amino protecting group, $C_1$ to $C_{12}$ acyl, $C_3$ to $C_{10}$ cycloalkyl, $C_3$ to $C_6$ heterocycle, $C_1$ to $C_{12}$ alkyl, $C_1$ to $C_{12}$ substituted alkyl, $C_7$ to $C_{16}$ alkylaryl, $C_7$ to $C_{16}$ substituted alkylaryl, a $C_6$ to $C_{15}$ alkyl heterocycle, or a substituted $C_6$ to $C_{15}$ alkyl heterocycle; $R_{16}$ is optionally present as a $C_1$ to $C_{18}$ substituent group when $R_1$ and $R_2$ are other than a hydrogen atom or an amino protecting group;

Wherein said library of compounds is composed of SL physically separate sublibraries; wherein SL is equal to (2B+4);

Further wherein each sublibrary is composed of physically separate mixtures, wherein the number of said mixtures is equal to the number of different substituents incorporated at $R_{fix}$, which $R_{fix}$ can be any one of $R_{19}$, $R_{20}$, $R_{21}$, $R_{22}$, $R_{23}$, or $R_{24}$ in the above Formula IV;

Wherein the compounds of the above Formula IV are synthesized and tested as follows:

(a) For each sublibrary SL, choosing $R_{fix}$ from $R_{19}$, $R_{20}$, $R_{21}$, $R_{22}$, $R_{23}$, or $R_{24}$;

(b) Dividing a solid support into approximately equal separate portions with the number of portions equal to the number of substituents to be incorporated at $R_{23}$, and couple each physically separate portions of solid support to one of the monomers containing a single substituent at $R_{23}$, then mixing all of said physically separate portions;

(c) Dividing the mixed solid support from step (a) into approximately equal separate portions in a number equal to the number of different substituents to be incorporated at $R_{24}$ by alkylation, alkylating each physically separate solid support mixtures with one alkyl group, then mixing said resins;

(d) When B is 1 through 3, dividing each of said solid support portions into a number of approximately equal separate portions, said number equal to the number of substituents at $R_{21}$, coupling one of the monomers containing a single substituent $R_{23}$ to each separate solid support portion then mixing said portions;

(e) When B is 1 to 3, separating said mixture of solid support portions into a number of approximately equal separate portions, said number equal to the number of alkyl substituents at $R_{20}$, alkylating each physically separate portion with one such alkylating agent, and mixing all the resultant solid support portions;

(f) Optionally repeating steps (d) and (e) one or two times when B is two or three, respectively;

(g) Dividing the mixture of solid support portions from either step (c), (e), or step (f) into approximately equal separate portions equal to the number of substituents to be placed at $R_{19}$, coupling one such monomer containing a single $R_{19}$ to each physically separate solid support portion, and mixing said portions;

(h) Dividing the mixture of portions from step (g) into a number of approximately equal separate portions, said number equal to the number of alkyl substituents at $R_{22}$ to be utilized, alkylating each said separate portion with a single alkyl group $R_{22}$;

(i) Optionally adding $R_{17}$ and/or $R_{18}$ by reductive alkylation;

(j) Optionally adding the quaternary substituent $R_{16}$;

(k) Optionally reducing the interior amides, thus converting X and Y taken together are a carbonyl oxygen to wherein each X and Y is a hydrogen atom; and (l) Cleaving said molecules from the solid support;

(m) Testing each portion of each SL sublibraries in the appropriate biological screen or screens; and determining from the results of said screens which substitutent at $R_{fix}$ is the best.

(n) Optionally synthesizing the molecule of Formula (I) containing the best ($R_{fix}$) substitutent at $R_{19}$, $R_{20}$, $R_{21}$, $R_{22}$, $R_{23}$, or $R_{24}$;

With the proviso that for each sublibrary SL the first solid support mixing step immediately following the introduction of $R_{fix}$ is omitted;

Further wherein:

(1) each coupling step in the above series of steps ((b), (d), (f) and (g)) involves a substrate of the Formula (V):

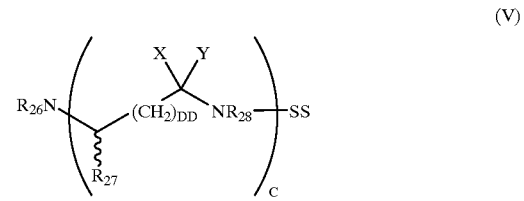

With an excess of an active acylating form of the monomer of the Formula (VI):

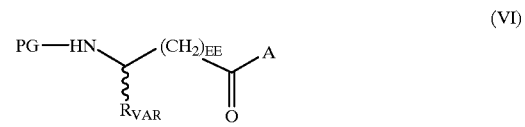

Wherein in the above Formulas (V) and (VI):

SS is a solid support;

$R_{26}$ are two hydrogen atoms each bound to the nitrogen atom;

$R_{28}$ is a $C_1$ to $C_{18}$ substituent group;

$R_{27}$ is independently a hydrogen atom, $C_1$ to $C_{12}$ alkyl, $C_1$ to $C_{12}$ substituted alkyl, phenyl, substituted phenyl, $C_7$ to $C_{16}$ alkylaryl, $C_7$ to $C_{16}$ substitued alkylaryl, a $C_6$ to $C_{15}$ alkyl heterocycle, or a substituted $C_6$ to $C_{15}$ alkyl heterocycle;

$R_{VAR}$ can be the same or different as $R_{27}$ and is chosen from the same group of substituents as $R_{27}$;

DD and EE are independently 0 to 5;

X and Y are either taken together to form a carbonyl oxygen;

PG is an amino protecting group other than trityl;

A is a group, when taken with the preceeding carbonyl group; that forms an active acylating agent; and C is from 0 to 4;

(2) Each alkylating step in the above steps (c), (e), (f) and (h) requires reacting a substrate of the Formula (VII):

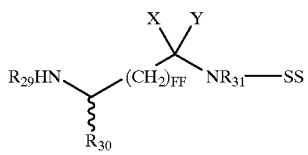

(VII)

With an excess of an alkylating agent of the Formula (VIII):

(LG)-Q          (VIII)

Under anhydrous conditions, and an inert atmosphere in a polar, aprotic solvent;

Wherein in the above Formulas (VII) and (VIII):

LG is a leaving group under the conditions of the alkylation;

Q is a $C_1$ to $C_{18}$ substituent group as defined above in Formula (I);

FF is 0 to 5;

X and Y are taken together to form a carbonyl oxygen;

$R_{31}$ is a hydrogen atom when $R_{29}$ is a trityl group or is a $C_1$ to $C_{18}$ substituent group;

$R_{30}$ is independently a hydrogen atom, $C_1$ to $C_{12}$ alkyl, $C_1$ to $C_{12}$ substituted alkyl, phenyl, substituted phenyl, $C_7$ to $C_{16}$ alkylaryl, $C_7$ to $C_{16}$ substitued alkylaryl, a $C_6$ to $C_{15}$ alkyl heterocycle, or a substituted $C_6$ to $C_{15}$ alkyl heterocycle; and $R_{29}$ is a trityl group when $R_{31}$ is a hydrogen atom or is a group of the Formula (IX):

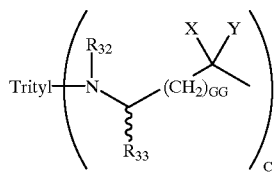

(IX)

Wherein in the above Formula (IX):

X and Y are as X and Y above;

GG is 0 to 5;

C is from 1 to 4;

$R_{33}$ is independently a hydrogen atom, $C_1$ to $C_{12}$ alkyl, $C_1$ to $C_{12}$ substituted alkyl, phenyl, substituted phenyl, $C_7$ to $C_{16}$ alkylaryl, $C_7$ to $C_{16}$ substitued alkylaryl, a $C_6$ to $C_{15}$ alkyl heterocycle, or a substituted $C_6$ to $C_{15}$ alkyl heterocycle; and $R_{32}$ is a hydrogen atom if $R_{32}$ is bonded to the N-terminal amino group or otherwise it is a $C_1$ to $C_{18}$ substituent wherein one such $C_1$ to $C_{18}$ substituent differs from the other substituents;

(3) Reductive alkylation of the N-terminal nitrogen group as described above in step (i) of a compound of the Formula (X):

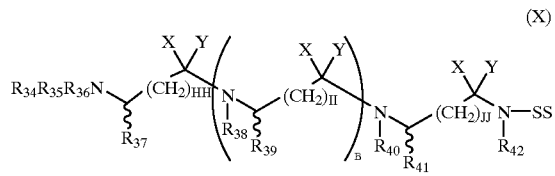

(X)

Under mildly acidic conditions with a ketone or aldehyde containing the $R_{34}$ and/or $R_{35}$ groups followed by the treatment of a reducing agent;

Wherein in the above Formula (X):

X and Y are taken together to form a carbonyl oxygen;

HH, II, and JJ are independently 0 to 5;

B is from 0 to 3;

$R_{39}$, $R_{41}$ and $R_{37}$ are the same or different and are chosen from the group consisting of independently a hydrogen atom, $C_1$ to $C_{12}$ alkyl, $C_1$ to $C_{12}$ substituted alkyl, phenyl, substituted phenyl, $C_7$ to $C_{16}$ alkylaryl, $C_7$ to $C_{16}$ substitued alkylaryl, a $C_6$ to $C_{15}$ alkyl heterocycle, or a substituted $C_6$ to $C_{15}$ alkyl heterocycle;

$R_{40}$ and $R_{42}$ are different and are a $C_1$ to $C_{18}$ substituent group;

$R_{34}$ or $R_{35}$ when B is 0, is optionally one or two hydrogen atoms attached to the nitrogen atom, or is a optionally one or more, same or different groups, chosen from the group consisting of a hydrogen atom, an amino protecting group, $C_1$ to $C_{12}$ acyl, $C_3$ to $C_{10}$ cycloalkyl, $C_3$ to $C_6$ heterocycle, $C_1$ to $C_{12}$ alkyl, $C_1$ to $C_{12}$ substituted alkyl, $C_7$ to $C_{16}$ alkylaryl, $C_7$ to $C_{16}$ substituted alkylaryl, a $C_6$ to $C_{15}$ alkyl heterocycle, or a substituted $C_6$ to $C_{15}$ alkyl heterocycle;

$R_{36}$ is a hydrogen or a bond to a $R_{34}$ or $R_{35}$ before the reduction occurs, and when B is from 1 to 3; $R_{38}$ is a $C_1$ to $C_{18}$ substituent group different from at least one other $R_{40}$, $R_{42}$ or $R_{38}$ groups;

(4) Optional reduction of the amide bonds as described above in step (j) of a compound of Formula (X) wherein X and Y are taken together to form a carbonyl groups, before or after it is cleaved from the solid support, using a boron reducing agent.

(5) Optionally quaternization of the terminal amino groups with an excess amount of alkylating agent of above of the formula:

(LG)-Q

Where (LG) and Q have the same meanings as above in a polar, aprotic solvent.

It will be obvious to one skilled in the art that, in the above positional scanning method, the substituents at $R_{34}$, $R_{35}$ and $R_{36}$ can be designated as "$R_{fix}$", such that the number of sublibraries SL would be increased by one, two or three, respectively, depending on how many of these three "R" groups are varied.

Yet another aspect of the invention is an iterative synthetic approach wherein the method for the iterative synthesis and screening of a library of an approximately equimolar amount of compounds of the Formula (XI):

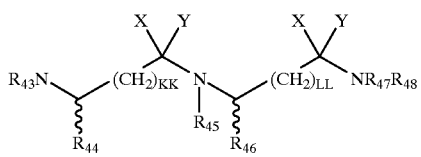

(XI)

Wherein in the above Formula (XI):

$R_{48}$ is a hydrogen atom or a solid support;

$R_{45}$ and $R_{47}$ are different and are each a $C_1$ to $C_{18}$ substituent group;

KK and LL are independently 0 to 5;

$R_{44}$ and $R_{46}$ are independently chosen from the group consisting of independently a hydrogen atom, $C_1$ to $C_{12}$ alkyl, $C_1$ to $C_{12}$ substituted alkyl, phenyl, substituted phenyl, $C_7$ to $C_{16}$ alkylaryl, $C_7$ to $C_{16}$ substitued alkylaryl, a $C_6$ to $C_{15}$ alkyl heterocycle, or a substituted $C_6$ to $C_{15}$ alkyl heterocycle;

X and Y are either taken together to form a carbonyl group or are separate and are each a hydrogen atom;

$R_{43}$ is one or two hydrogen atoms, or groups of the formula $R_a$, $R_b$ and $R_c$, wherein $R_a$ and $R_b$ independently are a hydrogen atom, an amino protecting group, $C_1$ to $C_{12}$ acyl, $C_3$ to $C_{10}$ cycloalkyl, $C_3$ to $C_6$ heterocycle, $C_1$ to $C_{12}$ alkyl, $C_1$ to $C_{12}$ substituted alkyl, $C_7$ to $C_{16}$ alkylaryl, $C_7$ to $C_{16}$ substitued alkylaryl, a $C_6$ to $C_{15}$ alkyl heterocycle, or a substituted $C_6$ to $C_{15}$ alkyl heterocycle; $R_c$ is optionally present as a $C_1$ to $C_{18}$ substituent group when $R_a$ and $R_b$ are other than a hydrogen atom or an amino protecting group; and Wherein the method comprises:

(a) Splitting a solid support into a number of approximately equal, separate portions, the number of said portions being equal to the number of monomers containing different substituent groups at $R_{46}$;

(b) Coupling a monomer containing one of the number of substituent groups at $R_{46}$ to a separate portion of the solid support;

(c) Mixing all of the separate portions of solid support;

(d) Splitting the solid support mixture into approximately equal, separate portions, the number of portions equal to the number of different substituents to be added at $R_{47}$;

(e) Alkylating each separate portion of solid support with a single alkylating agent, each agent containing a unique alkyl group at $R_{47}$, thus adding a single alkyl group at $R_{47}$ to the plurality of the compounds bonded to each separate portion of solid support;

(f) Mixing all of the separate portions of solid support;

(g) Splitting the solid support mixture into a number of approximately equal separate portions, the number of said portions equal to the number of different substituents to be added at $R_{44}$;

(h) Coupling each monomer containing a single substituent group at $R_{44}$ to a separate portion of the solid support, thus coupling a single different monomer to the plurality of the compounds bonded to each separate portion of the resin;

(i) Splitting each of the separate portions of solid support into a number of approximately equal physically-separate portions, wherein the number of portions is equal to the number of different substituents to be added by alkylation at $R_{45}$;

(j) Alkylating each separate portion of solid support with a separate alkylating agent containing a single different $R_{45}$ group, thus adding a single different alkyl group at $R_{45}$ to the plurality of the compound bonded to each separate portion of the resin;

(k) Cleaving the generated compound mixtures of Formula (XI) from each separate portion of solid support and testing each separate mixture from each separate portion of solid support in the appropriate biological screen or screens, and determining from the results of said screens which mixture contains the best combination of substituents at $R_{44}$ and $R_{45}$;

(l) Repeating steps (a) through (e), wherein the substituents at $R_{46}$ and $R_{47}$ are the same used in said original steps (a) through (e);

(m) Coupling the monomer containing the most active $R_{44}$ substituent to each of the separate portions of resin from step (l);

(n) Alkylating each of the portions from step (m) with the best alkyl group at $R_{45}$ determined in step (k);

(o) Cleaving each separate mixture of compounds of the above Formula (XI) from the solid support, testing each separate mixture of compounds in the same biological screens as in step (k), and determining the most active substituent at $R_{47}$ in those screens;

(p) Repeating steps (a) and (b), wherein the same group of monomers containing the various substituent $R_{46}$ are used as in the original step (a);

(q) Alkylating each separate resin portion from step (p) with an alkylating agent placing the best alkyl group at $R_{47}$ as such alkyl group was determined in step (o);

(r) Coupling to each separate portion of resin the monomer containing the best $R_{44}$ substituent as such substituent was determined in step (k);

(s) Alkylating each separate portion of resin with a group that was the best alkyl group $R_{45}$ as such group determined in step (k);

(t) Cleaving each separate compound from the solid support, and testing each separate mixture of compound separately in the same screens as in steps (o) and (k) in order to determine the best substituents at $R_{46}$;

(aa) Optionally reductively alkylating and quaternizing the N-terminal amino group ($R_{43}$), either before or after cleavage of the compound from the solid support; and (bb) Optionally reducing the interior amide groups before or after cleavage of the compound from the solid support such that X and Y in Formula (XI) are each a hydrogen atom;

Further wherein:

(1) each of the above coupling steps (b), (h), (l), (m), (p) or (r), involves a substrate of the Formula (XII):

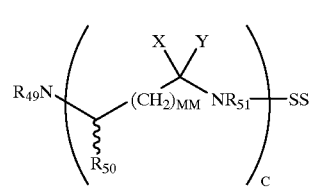

(XII)

With an excess of an active acylating form of the monomer of the Formula (XIII):

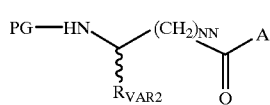

(XIII)

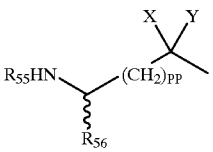

(XVI)

Wherein in the above Formulas (XII) and (XIII):
SS is a solid support;
$R_{49}$ is two hydrogen atoms;
$R_{51}$ is a $C_1$ to $C_{18}$ substituent group
$R_{50}$ is independently a hydrogen atom, $C_1$ to $C_{12}$ alkyl, $C_1$ to $C_{12}$ substituted alkyl, phenyl, substituted phenyl, $C_7$ to $C_{16}$ alkylaryl, $C_7$ to $C_{16}$ substitued alkylaryl, a $C_6$ to $C_{15}$ alkyl heterocycle, or a substituted $C_6$ to $C_{15}$ alkyl heterocycle;
$R_{VAR2}$ can be the same or different as $R_{50}$ and is chosen from the same group of substituents as $R_{50}$;
MM and NN are independently 0 to 5;
X and Y are either taken together to form a carbonyl group or are separate and are each a hydrogen atom;
PG is an amino protecting group other than trityl;
A is a group, when taken with the preceeding carbonyl group; that forms an active acylating agent; and
C is 0 or 1;

(2) Each of the above alkylating steps (e), (j), (l), (m), (q) and (s), requires reacting a substrate of the Formula (XIV):

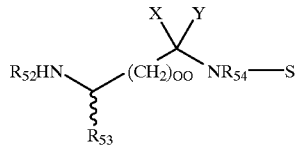

(XIV)

With an excess of an alkylating agent of the Formula (XV):

(LG)-Q (XV)

Under anhydrous conditions, and an inert atmosphere in a polar, aprotic solvent;
Wherein in the above Formulas (XIV) and (XV):
LG is a leaving group under the conditions of the alkylation;
Q is a $C_1$ to $C_{18}$ substituent group;
OO is 0 to 5;
X and Y are taken together to form a carbonyl group; or are separate and are each a hydrogen atom;
$R_{54}$ is a hydrogen atom if $R_{52}$ is a trityl group or is a $C_1$ to $C_{18}$ substituent group;
$R_{53}$ is independently a hydrogen atom, $C_1$ to $C_{12}$ alkyl, $C_1$ to $C_{12}$ substituted alkyl, phenyl, substituted phenyl, $C_7$ to $C_{16}$ alkylaryl, $C_7$ to $C_{16}$ substitued alkylaryl, a $C_6$ to $C_{15}$ alkyl heterocycle, or a substituted $C_6$ to $C_{15}$ alkyl heterocycle;
$R_{52}$ is a trityl group if $R_{54}$ is a hydrogen atom or is a group of the Formula (XVI):

Wherein in the above Formula (XVI):
X and Y are as X and Y above;
PP is 0 to 5;
$R_{55}$ is a trityl group;
$R_{56}$ is independently a hydrogen atom, $C_1$ to $C_{12}$ alkyl, $C_1$ to $C_{12}$ substituted alkyl, phenyl, substituted phenyl, $C_7$ to $C_{16}$ alkylaryl, $C_7$ to $C_{16}$ substitued alkylaryl, a $C_6$ to $C_{15}$ alkyl heterocycle, or a substituted $C_6$ to $C_{15}$ alkyl heterocycle; and (3) Optional reductive alkylation of the N-terminal nitrogen group of a compound of the Formula (XVII):

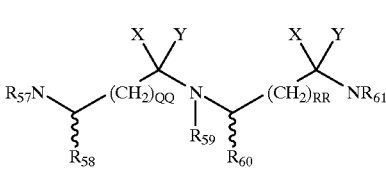

(XVII)

Under mildly acidic conditions with a ketone or aldehyde containing the $R_1$ and/or $R_2$ groups followed by treatment with a reducing agent;
Wherein in the above Formula (XVII):
X and Y are taken together to form a carbonyl group;
QQ and RR are independently 0 to 5;
$R_{58}$ and $R_{60}$ are the same or different and are chosen from the group consisting of independently of a hydrogen atom, $C_1$ to $C_{12}$ alkyl, $C_1$ to $C_{12}$ substituted alkyl, phenyl, substituted phenyl, $C_7$ to $C_{16}$ alkylaryl, $C_7$ to $C_{16}$ substitued alkylaryl, a $C_6$ to $C_{15}$ alkyl heterocycle, or a substituted $C_6$ to $C_{15}$ alkyl heterocycle;
$R_{59}$ and $R_{61}$ are the same or different and are a $C_1$ to $C_{18}$ substituent group;
$R_{57}$ is either two hydrogen atoms attached to the nitrogen atom, or is a single hydrogen atom and another group bonded to the nitrogen atom which groups is selected from the group consisting of a hydrogen atom, an amino protecting group, $C_1$ to $C_{12}$ acyl, $C_3$ to $C_{10}$ cycloalkyl, $C_3$ to $C_6$ heterocycle, $C_1$ to $C_{12}$ alkyl, $C_1$ to $C_{12}$ substituted alkyl, $C_7$ to $C_{16}$ alkylaryl, $C_7$ to $C_{16}$ substitued alkylaryl, a $C_6$ to $C_{15}$ alkyl heterocycle, or a substituted $C_6$ to $C_{15}$ alkyl heterocycle;

(4) Optional reduction of the amide bonds of a compound of Formula (XI), before or after it is cleaved from the solid support, using a boron-based reducing agent, such as borane or sodium borohydride, and the like.

In the above iterative synthetic approach, it would be obvious to one skilled in the art the method could easily be extended to encompass a library of all of the compounds of Formula I, in other words, such that repeating the coupling; alkylation and testing steps described above be applied to compounds within the scope of Formula I, wherein B is 1, 2, or 3. Furthermore, it would be obvious to one skilled in the art that substitutent at $R_1$, $R_2$ and $R_{10}$ would be separate variables that could be synthesized and screened by the above iterative method. Due to their location in the molecule, these substituents, if present, would be screened to find the best substituent before the N-terminal monomer and the attendant N-alkyl group could be determined.

Finally, one skilled in the art would be able to combine the above iterative and positional scanning approaches in order to conserve resources and time. For example, in libraries where B in the above Formula I is 1, 2, or 3, the iterative approach could be used to determine the optimum substituents on the last two variable substituents and the optimum substituents at the remaining positions could be determined by the positional scanning approach.

Simultaneous multiple solid phase methodology (Merrifield, R. B., *J. Am. Chem. Soc.*, 85:2149 (1963)) was the basic technology used to synthesize and design the peptidomimetic library set forth in Formula I. A solid phase-based synthetic method was developed to successively alkylate each amide bond following its formation. In this library, different alkylating agents were used to create increased molecular diversity and to eliminate the hydrogen bonding potential of the amide functionality. Optionally, the N-terminal nitrogen can be reductively alkylated and quarternized and the interior amide bonds can be reduced (i.e., X and Y are each a hydrogen atom). In Formula I, when B is 2 or 3, $R_4$ and $R_5$ do not have to be the same as the other $R_4$ and $R_5$ groups present in the molecule. Cleavage from the solid support led to peptidomimetics of the Formula I (wherein $R_9$ is hydrogen, each having diversity positions at the amino acid side chain positions ($R_3$, $R_5$ and $R_7$), at the amide alkyl groups ($R_4$, $R_6$, $R_8$), and at the N-terminal groups ($R_1$, $R_2$ and $R_{10}$).

Although a number of methods for the permethylation of peptides in solution (Hakomori, S. -I., *J. Biochem* 55:205 (1964); Vilkas, E., et al., *Tetrahedron Letters*, 26:3089 (1968); Challis, B. C., et al., *The Chemistry of Amides*, Zabicky, J. Ed.; Interscience: New York, 1970, pp. 731–857; are known, the permethylation of resin-bound peptides, using sodium hydride for the formation of amide anions, was reported only recently (Ostresh et al., *Proc. Natl. Acad. Sci. USA* 91:11138–11142 (1994)). For the purpose of a stepwise alkylation following each amino acid coupling on the solid support, lithium t-butoxide was found to be more effective for the successive formation of the amide anions.

As an important prerequisite for the synthesis of this library, reproducible conditions for the N-amide alkylations had to be established for the base treatment of solid phase-bound amino acids or peptides. The reactions were carried out under an anhydrous nitrogen atmosphere, and the amino acid or peptide resin of interest was treated with excess lithium t-butoxide in tetrahydrofuran. Following removal of excess base, the alkylating agent in an aprotic, polar solvent such as dimethyl sulfoxide was reacted with the resin-bound compound. The alkylation reaction mixture was then removed and the base and alkylation treatments were repeated to drive the alkylation reaction to completion. Potential racemization during alkylation was studied using analytical reversed-phase high performance liquid chromatography (RP-HPLC); the four possible permethylated stereoisomers of Phe-Leu-NH$_2$ were used as reference standards. (Ostresh, J. M., et al., *Peptides 94; Proceedings of the 23rd European Peptide Symmosium*, Maia, H. L. S. Ed.; Escom: Leiden, 1995, pp. 416–417). The maximum percentage of racemization found following repeated base and methylation treatments was <1%.

The techniques for the synthesis of the selectively N-alkylated compounds of Formula I are well known in the art, with the exception of the selective N-alkylation procedures discussed above. These techniques can be conveniently discussed in conjunction with Scheme 1:

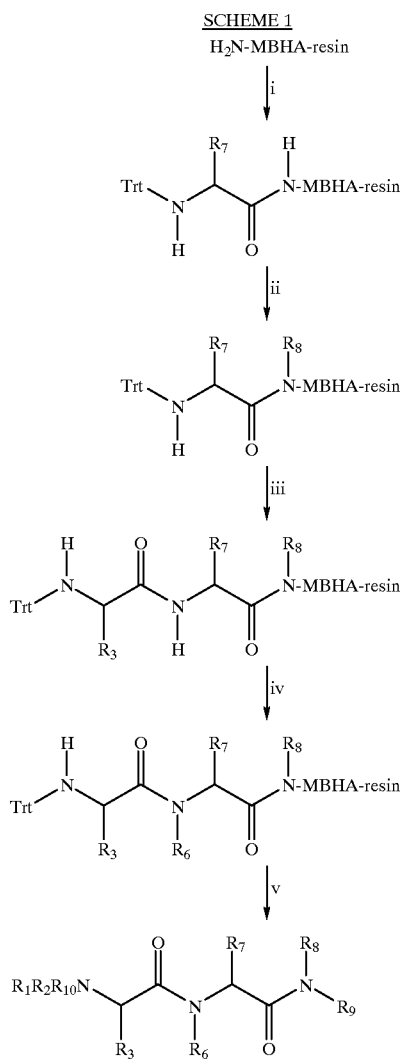

In the above Scheme 1, Reaction "i" represents the coupling of the C-terminus of peptide-like residue to an amino-derivatized solid support. For instance, an peptide-like residue with amino terminus protected by a base or weak-acid labile protecting group, such as Fmoc, is converted to a good acylating agent in situ using known reagents and conditions. Such reagents include carbodiimide reagents (eg. N,N'-dicyclohexylcarbodiimide (DCC) and N,N'-diisopropylcarbodiimide in conjunction with 1-hydroxybenzotriazole) in an aprotic, polar solvent such as DMF. (Such couplings were repeated if necessary.) In the reaction labelled as "ii" in Scheme 1, the N-terminal protecting group was removed and replaced with a trityl group, which was found to protect such group during the next interior, selective N-alkylation step. Under anhydrous conditions and an inert atmosphere, the tritylated residue was treated with an excess amount of lithium t-butoxide in a polar, aprotic solvent (such as tetrahydrofuran), followed by the addition of an excess of an alkylating agent of the formula (LG)-Q wherein LG is a good leaving group under the S$_n$2 conditions of the reaction (such as bromo, iodo, tosyl, triflate and the like), and Q forms a $C_1$ to $C_{18}$ linear, branched, cyclic, saturated, partially or fully unsaturated alkyl group, as described above in conjuction with the "$C_1$ to $C_{18}$ substituent group" of $R_4$, $R_6$, and $R_8$ of Formula I. Multiple repetitions of such alkylating conditions are often necessary. The reaction denoted as "iii" in the above Scheme 1 denotes the steps necessary to couple a second (and any additional) monomer (as defined in Formula II) the recently N-alkylated resin-bound residue. Thus, the trityl protecting group is removed under weakly acidic conditions (2% trifluoroacetic acid), the deprotected molecule neutralized then coupled with and FMOC-protected amino acid (or one bearing an equivalent protecting group) using the same conditions for coupling the first residue to the amino-deriviatized resin. The reaction labelled "iv" in Scheme 1 is a repeat of the selective N-alkylation procedure, including the preliminary N-protection steps, of reaction "ii". Reaction "v" shows the removal of the trityl group from the amino-terminus of the bound residue as before followed by the removal of the selectively-N-alkylated molecule from the amino-derivatized residue with hydrogen fluoride. One skilled in the art would recognize that subsequent residues could be added then selectively alkylated before removal of the amino-derivatized according to the steps set forth in Scheme 1, thus yielding compounds of Formula I wherein B is 1, 2 or 3. Furthermore, while still attached to the resin, it is advantages to derivatize the N-terminal amino group to form compounds wherein at least one of $R_1$ and $R_2$ is other than hydrogen, and where possibly $R_{10}$ is present. $R_1$ and $R_2$ groups are most frequently added by the process of reductive alkylation, as set forth (Borch, R. F., et al., *J. Am. Chem. Soc.*, 93:2897 (1971); Coy, D. H., et al., *Tetrahedron*, 44:835 (1988); Staňková, M., et al., *Drug Development Research*, 33:146 (1994)(herein incorporated by reference). Thus, appropriate aldehyde or ketone is added to the resin-bound compounds under mildly acidic conditions to effect Schiff-base (imine) formation, which imine is reduced to the substituted amine by sodium cyanoborohydride, or other mild reducing agent. Additionally, the free amino terminus can be acylated with a $C_1$ to $C_{12}$ acyl group, using well-known conditions as described in Staňková, M., et al., *Drug Development Research*, 33:146 (1994)(herein incorporated by reference). It is preferable, however, to add the $R_{10}$ (alkyl) substituent before reductive alkylation. Such an alkylation proceeds under the same alkylation conditions used for the $R_4$, $R_6$, and $R_8$ groups. Finally, while still resin-bound, or after cleavage from the resin, the interior amide groups can be reduced (i.e. X and Y taken together form a carbonyl group to X and Y are each a hydrogen atom.) Such a reduction is known in the art (see, for instance, Dooley, C. T., et al., *Analaesia, INRC Proceedings*, 1:400 (1995)). Thus, for both situations (i.e., when $R_9$ is a hydrogen atom or a solid (resin)) mild, soluble hydrogenation catalysts such as a boric acid/trimethylborate/borane-tetrahydrofuran combination can be used.

Individual model compounds were used to study the modification of amino acid side chains during the alkylation conditions. Fifty N-trityl (triphenylmethyl; Trt) dipeptide resins, designated Trt-O-Leu-MBHA resin (MBHA=p-methylbenzhydrylamine) were alkylated where O represents a single proteinogenic L-amino acid, their D-counterparts, or 11 other individual "unnatural" amino acids. Aspartic acid was excluded from the 20 proteinogenic amino acids, since multiple products were formed following base treatment and alkylation. Methyl iodide, allyl bromide and benzyl bromide were used initially as alkylating agents. The individual crude alkylated products were analyzed by RP-HPLC and matrix assisted laser desorption ionization-mass spectroscopy (MALDI-MS) to determine their purity and identity. (Ostresh, J. M., et al., *Peptides 94: Proceedings of the 23rd European Peptide Symposium,* Maia, H. L. S. Ed.; Escom: Leiden, 1995, pp. 463–464). During the alkylation procedure, the functional groups of the amino acid side chains were reproducibly modified. Based on preliminary evidence the following modifications were observed: 1) the ε-monoalkyl amine was formed during alkylation when the e-amino group of lysine was protected with Boc; 2) the unprotected amide functionality of the side chains of L-asparagine and L-glutamine, when alkylated with any of the three alkylating agents, yielded dialkyl amides, whereas allylation and benzylation of the D-isomers led to mono and dialkyl amides, indicating stereochemical hindrance of the diastereomers; 3) the 2,2,5,7,8-pentamethylchroman-6-sulfonyl (Pmc) protected arginine side chain yielded the trimethyl derivative following permethylation and di- and triallyl derivatives following perallylation, but was negligibly alkylated following perbenzylation; 4) when unprotected, the reactive indole nitrogen of tryptophan was alkylated; 5) the use of 2-bromo-Cbz protection for tyrosine resulted in formation of the methyl and allyl ether analogs and any O-benzyl products formed using benzyl bromide in the alkylation were cleaved during the hydrogen fluoride treatment; and 6) when tyrosine hydroxyl was t-Bu protected, the side chain was unmodified. Although not studied in detail, glutamic acid t-Bu ester led to multiple products following repeated alkylations. Other amino acid derivatives having side chains with potentially reactive functionalities, including serine, threonine, hydroxyproline (all protected as their t-Bu ether), methionine (sulfoxide), and tryptophan (Boc), did not undergo any modification during the alkylation step. Repetitive alkylations of trityl-protected N-terminal glycine and β-alanine led to side products containing additional alkyl groups as detected by MALDI-MS.

The combinatorial library of compounds of Formula I (wherein B=0) has an OOXX format, where O represents a defined position and X represents a mixture position. Forty-six different amino acids (cysteine and histidine were excluded since analogs containing these amino acids were found to have significant side reactions and/or incomplete reaction during the alkylation procedure) were incorporated into the first X position ($R_3$), and 50 different amino acids were incorporated into the first O position ($R_7$). The amide alkyl groups in the second X ($R_8$) and second O positions ($R_6$) were: methyl, ethyl, allyl, benzyl or naphthylmethyl. This combinatorial library consists of 250 mixtures (50 amino acids×5 alkyl groups), each of which is composed of 230 compounds (46 amino acids×5 alkyl groups), and was prepared applying the divide, couple and recombine process, also independently reported as the "mixing and portioning" and "split synthesis" approaches (Lam, K. S., et al., *Nature*, 354:82 (1991); Furka, A., et al., *Int. J. Pept. Protein Res.*, 37:487 (1991)). The stepwise synthesis was carried out on the solid phase by alternating amino acid attachment and alkylation of the previously formed amide bond as outlined in FIG. 1. Standard Fmoc chemistry for the incorporation of amino acids was used with MBHA resin as the solid support. Alkylation of the amide bond between the C-terminal amino acid and the MBHA linker was found to significantly decrease the stability of the amide-resin linkage to acidolytic conditions. (Kornreich, W., et al., *Int. J. Pept. Protein Res.*, 25:414 (1985)). The amino groups were protected with the bulky trityl group to avoid modification of the N-terminal amine during the manipulation of the amide groups of the resin-bound compounds. The five alkyl halides [methyl iodide, ethyl iodide, allyl bromide, benzyl bromide, and 2-(bromomethyl)naphthalene] were reacted with the previously formed amide anions using repeated treatments of the alkylation method described above. Replicates of control resins Trt-Leu-MBHA and Trt-Trp-MBHA were added during each of the five separate alkylation treatments on the solid phase resins. The $R_8$ residues were introduced at the same time, enabling the completeness of each of these reactions to be determined. A second amino acid derivative was then coupled to these control resins following removal of the trityl group with 2% trifluoroacetic acid in dichloromethane. This resulted in the generation of individual compounds having the formulas $H_2N$-Phe-Leu-NHR and $H_2N$-Ala-Trp(R)-NHR (R=methyl, ethyl, allyl, benzyl, or naphthylmethyl). No starting material was detected by RP-HPLC for the crude compounds following three treatments with methyl iodide and ethyl iodide. Allylation, benzylation and naphthylmethylation required six repetitions of the alkylation procedure, with generally less than 10% starting material remaining (as determined by RP-HPLC). In case of the Ala-Trp controls up to 40% of monoalkylated material was seen (using RP-HPLC). The 230 resins containing the first two library positions were then combined, thoroughly mixed and divided into 250 equal portions (50×5 library resin packets). Following trityl removal, the second group of protected amino acids was added (cysteine and histidine included), the Fmoc group was removed, and the free amino groups were again reacted with trityl chloride. The newly formed amide bond was then alkylated as described above, with the exception that five repetitions of the alkylation procedure were carried out. For this second alkylation step, control resins were prepared having the formula Trt-Phe-Leu-NHMe-MBHA and Trt-Ala-Trp-NHMe-MBHA. These control resins were permethylated at the first amide position to determine the completeness of the second alkylation. Following trityl removal, starting material was not detected by RP-HPLC or MALDI-MS for any of the five crude alkylation control products. The highly acid labile amide linkage between the peptidomimetic and the MBHA resin linker does not permit the acid labile side chain protecting groups to be removed prior to final cleavage from the resin. Thus, the mixtures were cleaved from the resin under standard high hydrogen fluoride cleavage conditions (Houghten, R. A., et al., *Int J. Pept. Protein Res.*, 27:673 (1986)) and obtained as lyophilized powders following extraction with 50% aqueous acetonitrile. The yields of some of the crude control compounds were found to be sequence-dependent. During the final acidic Trt removal, compounds having bulky alkyl residues in position $R_2$ were partially cleaved from the resin. (Gisin, B. F., et al., *J. Am. Chem. Soc.*, 94:3102 (1972)).

Compounds of the formula $H_2N$-Phe-N(R)-Leu-NHMe (R=methyl, ethyl, allyl, benzyl or naphthylmethyl) were individually synthesized using the described method to provide material as analytical controls. Following purification by preparative RP-HPLC, the identity of each compound was confirmed by RP-HPLC, MALDI-MS, HR-MS, microanalysis, and NMR.

The nonsupport-bound library mixtures were screened in solution in radio-receptor, antimicrobial and enzyme inhibition assays. Deconvolution of the highly active mixtures was carried out by both iterative and positional scanning methods. The iterative method is set forth in Dooley, et al., *Science*, 266:2019–2022 (1994) and the positional scanning method is set forth in U.S. patent application Ser. No. 07/943,709, herein incorporated by reference.

The immediately preceeding description sets forth in general the reaction techniques utilized in synthesizing the selectively N-alkylated compounds of Formula I. These techniques can be utilize in one of two strategic approaches for finding the most active compound; the iterative approach or the positional scanning approach. The iterative approach is well-known and is set forth in general in Houghten et al., *Nature*, 354, 84–86 (1991); and Dooley et al., *Science*, 266, 2019–2022 (1994); herein incorporated by reference. In the iterative approach, for example, sublibraries of a molecule having six variable groups are made wherein the first two variables are defined. (With reference to Figure, an example for this discussion would have B is 1, $R_{10}$ is absent, $R_1$ and $R_2$ are each a hydrogen atom, with $R_8$ through $R_3$ as the six variable groups.) Each of the compounds with the two defined variable groups is reacted with all of the other possibilites at the other four variable groups. These sublibraries are each tested to define the identity of the third varible in the sub-library having the highest activity in the screen of choice is determined. A new sub-library with the first three variable poisitions defined is reacted again with all the other possibilities at the remaining three undefined variable positions. As before, the identity of the fourth variable position in the sub-library having the highest activity is determined, and a new set of sub-libraries, with four defined variable regions, is synthesized. This process is repeated for all six variables, yielding the compound with each variable contributing to the highest desired activity in the screening pocess. Promising compounds from this process can then be synthesized on larger scale in traditional single-compound synthetic methods for further biological investigation.

The positional-scanning approach has been described for various organic libraries and for various peptide libraries (see, for example, R. Houghten et al. PCT/US91/08694, S. P. A. Fodor and L. Stryer and U.S. patent application Ser. No. 07/876,792, herein incorporated by reference). However, the positional-scanning approach has never been applied to the selectively N-alkylated compounds of the instant Formula I. In the positional scanning approach sublibraries are made defining only one variable with each set of sublibraries- and all possible sublibraires with each single variable defined (and all other possibilities at all of the other variable positions) is made and tested. From the instant description one skilled in the art could synthesize libraries wherein 2 fixed positions are defined at a time. From the testing of each single-variable defined library, the optimum substituent at that position is determined, pointing to the optimum or at least a series of compounds having a maximum of the desired biological activity. As this approach is applied to the selectively N-alkylated compounds of Formula I, sublibraries where each possibility of any one R group (e.g. $R_8$) is defined and all other possibilities of the remaining R groups are synthesized and screened for the desired activity. Thus, the number of sublibraries for compounds with a single position defined will be the number of different substituents desired at that position, and the number of all the compounds in each sublibrary will be the product of the number of substituents at each of the other varibles. Thus, the instant invention is directed to screening sublibraries of the selectively N-alkylated componds of Formula I wherein each sublibrary has an R group defined, and all other R groups are synthesized with the desired subtstituents, and defining each single variable in a similar grouping of sublibrairies and screening for biological activity, until all such variable positions have been defined and screened for the desired activity. One skilled in the art would realize that this approach could also be applied in the situation wherein each sublibrary has to R groups defined, using a modification of the above techniques.

The reduction of the interior amide of the compounds of Formula I is another means for the chemical transformation of such compounds which adds stability and can enhance activity. A number of reagents are available and well known for the reduction of amides to amines such as those disclosed in Wann et al., *JOC,* 46:257 (1981) and Raucher et al., *Tett.Let.,* 21:14061 (1980), both of which are incorporated herein by reference. Diborane has the advantage that trimethylborate, the only by-product in the reaction workup, is volatile and is therefore readily removed by evaporation in solution phase reduction. The use of excess diborane in refluxing tetrahydrofuran permits simple aliphatic and aromatic amides to be rapidly, and often quantitative be reduced into their corresponding amines.

A newly synthesized compound can be purified using a method such as reverse phase high performance liquid chromatography (RP-HPLC) or other methods of separation based on the size or charge of the compound. Furthermore, the purified compound can be characterized using these and other well known methods such as amino acid analysis and mass spectrometry.

After manufacture, the compounds can be assayed for receptor binding activity using the radioreceptor assay (Examples III and IV) or other assays outlined below, including the glycosidase assay (Example V).

Because some of the compounds of the present invention bind to the $\mu$ receptor, they can be used in in vitro assays to study the opiate receptor subtypes. For example, in a sample receptor of unknown type or origin, the compounds, after being labeled with a detectable marker such as a radioisotope, can be contacted with the receptor sample under conditions which specifically favor binding to a particular receptor subtype. Unbound receptor and compound can be removed, for example, by washing with a saline solution, and bound receptor can then be detected using methods well known to those skilled in the art. Therefore, the compounds of the present invention are useful in vitro for the diagnosis of relevant opioid receptor subtypes, and in particular the $\mu$ type, in brain and other tissue samples.

In addition to their utility in in vitro screening methods, the compounds are also useful in vivo. For example, certain of the instant compounds can be used in vivo diagnostically to localize opioid receptor subtypes. The compounds are also useful as drugs to treat pathologies associated with other compounds which interact with the opioid receptor system. It can be envisioned that these compounds can be used for therapeutic purposes to block the peripheral effects of a centrally acting pain killer. For instance, morphine is a centrally acting pain killer. Morphine, however, has a number of deleterious effects in the periphery which are not required for the desired analgesic effects, such as constipation and pruritus (itching). While it is known that the many peptides do not readily cross the blood-brain barrier and, therefore, elicit no central effect, the subject peptides can have value in blocking the periphery effects of morphine, such as constipation and pruritus.

This invention provides pharmaceutical compositions comprising the compounds of Formula I in a pharmaceutically acceptable carrier. As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents.

Suitable pharmaceutical carriers and their formulations are described in Martin, REMINGTON'S PHARMACEUTICAL SCIENCES, 15th Ed. (Mack Publishing Co., Easton 1975). Such compositions will, in general, contain an effective amount of the active reagent together with a suitable amount of carrier so as to prepare the proper dosage form for proper administration to the subject.

Useful pharmaceutical carriers for the preparation of the pharmaceutical compositions can be solids, liquids or gases. Thus, the compositions can take the form of tablets, pills, capsules, powders, enterically coated or other protected formulations (such as by binding on ion exchange resins or other carriers, or packaging in lipid protein vesicles or adding additional terminal amino acids), sustained release formulations, solutions (e.g. ophthalmic drops), suspensions, elixirs, aerosols, and the like. Water, saline, aqueous dextrose, and glycols are preferred liquid carriers, particularly (when isotonic) for injectable solutions. The carrier can be selected from various oils including those of petroleum, animal, vegetable or synthetic origin, for example, peanut oil, soybean oil, mineral oil, sesame oil, and the like. Suitable pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like.

The compositions may be subjected to conventional pharmaceutical procedures such as sterilization and may contain conventional pharmaceutical additives such as preservatives, stabilizing agents, wetting or emulsifying agents, salts for adjusting osmotic pressure, buffers, and the like.

This invention provides methods of effecting treating a mammal comprising the step of administering a therapeutically effective amount of a pharmaceutical composition of this invention to a subject. As used herein, the term "therapeutically effective amount" is that amount necessary to alleviate the condition from which the mammal suffers.

In the practice of the therapeutic methods of the present invention, an effective amount of a pharmaceutical composition of a compound of Formula I is administered via any of the usual and acceptable methods known in the art, either singly or in combination with another compound of the present invention. These compounds or compositions can thus be administered orally, sublingually, topically (e.g., on the skin or in the eyes), parenterally (e.g., intramuscularly, intravenously, subcutaneously or intradermally), or by inhalation, and in the form of either solid, liquid or gaseous dosage including tablets, suspensions, and aerosols, as is discussed in more detail above. The administration can be conducted in single unit dosage form with continuous therapy or in single dose therapy ad libitum.

In one embodiment, the therapeutic methods of the present invention are practiced when the relief of symptoms is specifically required or perhaps imminently so. In another embodiment, the method is effectively practiced as continuous or prophylactic treatment.

In the practice of the therapeutic methods of the invention, the particular dosage of pharmaceutical composition to be administered to the subject will depend on a variety of considerations including the nature of the disease, the severity thereof, the schedule of administration, the age and physical characteristics of the subject, and so forth. Proper dosages may be established using clinical approaches familiar to the medicinal arts. It is presently believed that dosages in the range 0.1 of 100 mg of a compound of this invention per kilogram of subject body weight will be useful, and a range of 1 to 100 mg per kg generally preferred where the administration is by injection or ingestion. Topical dosages may utilize formulations containing active peptides and a liquid carrier or excipient, with multiple daily applications being appropriate.

Fluorenylmethoxycarbonyl (Fmoc) amino acid derivatives were purchased from Calbiochem-Novabiochem Corp. (San Diego, Calif., USA), Bachem Bioscience Inc. (Philadelphia, Pa., USA) and Bachem California (Torrance, Calif., USA). MBHA resin, (1% divinylbenzene, 100–200 mesh, 0.9 mmol/g substitution), was received from Peninsula Laboratories, Inc (Belmont, Calif., USA). N,N'-Diisopropylcarbodiimide (DIC) and 1-hydroxybenzotriazole (HOBT) were purchased from Chem Impex International (Wood Dale, Ill., USA), trifluoroacetic acid from Halocarbon (River Edge, N.J., USA) and hydrogen fluoride from Air Products (San Marcos, Calif., USA). All other reagents and anhydrous solvents (DMSO, THF) were purchased from Aldrich Chemical Company (Milwaukee, Wis., USA). The solvents dichloromethane (DCM), dimethylformamide (DMF), isopropanol (IPA), and methanol were obtained from Fisher Scientific (Fair Lawn, N.J., USA). All reagents and solvents were used without further purification. MALDI-MS analyses were carried out on a Kratos Analytical Compact MALDI II (Ramsey, N.J., USA). HR-FAB-MS were recorded at the University of California Riverside Mass Spectrometry Facility, Department of Chemistry (Riverside, Calif., USA) on a ZAB mass spectrometer. Analytical RP-HPLC was performed on a Beckman System Gold instrument (Beckman Instruments, Fullerton, Calif., USA). Samples were analyzed using Vydac 218TP54 $C_{18}$ columns (0.46×25 cm). Preparative RP-HPLC purification was performed on a Waters Delta Prep 3000 instrument (Millipore, Waters Division, San Francisco, Calif., USA). Samples were purified using Waters Delta-Pak $C_{18}$ columns (2.5×10 cm). All gradients reported were linear in eluent A (0.05% TFA aqueous) and eluent B (0.05% TFA in acetonitrile); flow rates were 1 mL/min (analytical) and 20 mL/min (preparative); the eluent was monitored at 214 nm. Routine $^1$H NMR and $^{13}$C NMR spectra were recorded on a Varian Gemini 200 (200 MHz). Microanalyses were performed at Galbraith Laboratories, Inc. (Knoxville, Tenn., USA).

Library synthesis
Amino acid derivatives

The following amino acid derivatives were used in synthesizing a combinatorial library according to Formula I above: Fmoc-Ala-OH, Fmoc-Phe-OH, Fmoc-Gly-OH, Fmoc-Ile-OH, Fmoc-Lys(Boc)-OH, Fmoc-Leu-OH, Fmoc-Met(O)-OH, Fmoc-Asn-OH, Fmoc-Pro-OH, Fmoc-Gln-OH, Fmoc-Arg(Pmc)-OH, Fmoc-Ser(t-Bu)-OH, Fmoc-Thr(t-Bu)-OH, Fmoc-Val-OH, Fmoc-Trp(Boc)-OH, Fmoc-Trp-OH, Fmoc-Tyr(2BrCbz)-OH, Fmoc-Tyr(t-Bu)-OH, Fmoc-D-Ala-OH, Fmoc-D-Phe-OH, Fmoc-D-Ile-OH, Fmoc-D-Lys(Boc)-OH, Fmoc-D-Leu-OH, Fmoc-D-Asn-OH, Fmoc-D-Pro-OH, Fmoc-D-Gln-OH, Fmoc-D-Ser(t-Bu)-OH, Fmoc-D-Thr(t-Bu)-OH, Fmoc-D-Val-OH, Fmoc-D-Trp(Boc)-OH, Fmoc-D-Trp-OH, Fmoc-D-Tyr(t-Bu)-OH, Fmoc-D-Arg(Pmc)-OH, Fmoc-L-Nle-OH, Fmoc-D-Nle-OH, Fmoc-L-Nve-OH, Fmoc-D-Nve-OH, Fmoc-L-Nal-OH, Fmoc-D-Nal-OH, Fmoc-L-Phg-OH, Fmoc-L-Glu(t-Bu)-OH, Fmoc-D-Glu(t-Bu)-OH, Fmoc-β-Ala-OH, Fmoc-L-Cha-OH, Fmoc-D-Cha-OH, and Fmoc-Hyp(t-Bu)-OH.

Fmoc-Cys(MeOBn)-OH (MeOBn=4-methoxybenzyl), Fmoc-Cys(MeBn)-OH (MeBn=4-methylbenzyl), Fmoc-His(Trt)-OH and Fmoc-D-His(Trt)-OH were also used in the N-terminal position of the library.

EXAMPLE I
A. Synthesis of the combinatorial library
1. Coupling of the first amino acid derivative The library described below was synthesized using simultaneous multiple peptide synthesis (Houghten, R. A., Proc. Natl. Acad. Sci. USA, 82:5131 (1985). The solid support (MBHA resin) was contained in 230 polypropylene mesh packets (250 mg resin per packet; packet size 3 cm×3 cm). For use in the synthesis of control compounds, 40 additional polypropylene mesh packets were prepared containing MBHA resin (100 mg).

After the common wash and neutralization steps were carried out (1×DCM, 2×5% DIEA, 2×DCM, 2×DMF; approximately 8 mL per packet; all resin packets were completely covered with solvent) on all of the resin packets, the individual resin packets were separated into 46 groups, each containing five packets for the addition of the 46 amino acid derivatives used in the first coupling step. Fmoc-Leu-OH and Fmoc-Trp-OH were added to two groups of 20 control resin packets. Amino acid couplings were carried out on each of the 46 groups of five library resin packets by vigorously shaking 44 groups in a solution (67.5 mL) of 0.1 M Fmoc amino acid derivative (6.75 mmol)/DIC/HOBt in DMF overnight (Fmoc-Gly coupling required only 75 min); for the other two groups, library resin packets and control packets were vigorously shaken in a solution (175.5 mL) of 0.1 M Fmoc-L-Leu (17.55 mmol)/DIC/HOBt and 0.1 M of Fmoc-L-Trp (17.55 mmol)/DIC/HOBT in DMF overnight. The resin packets were washed (2×DMF, 1×DCM, 1×MeOH; approximately 8 mL per packet) and the completeness of amino acid coupling was verified using the ninhydrin test (Kaiser, E. T., et al., Anal. Biochem, 34:595 (1970)). The only amino acids which required repetitive couplings were Fmoc-L-Gln-OH, Fmoc-D-Gln-OH, Fmoc-L-Arg(Pmc)-OH and Fmoc-D-Lys(Boc)-OH. Removal of the Fmoc protecting group was accomplished by shaking the resin packets in 20% piperidine/DMF (1×3 min, 1×10 min; 2 L) followed by a wash cycle (5×DMF, 2×IPA, 3×DCM; approximately 8 mL per packet).

2. Tritylation of the N-terminal amino group

Following removal of the Fmoc group, the 270 resin packets (a total of 55 mmol of free N-α-amino groups) were shaken for 3 h in a 0.077 M solution of trityl chloride (276.75 mmol) in DCM/DMF (9:1, 3.6 L) containing diisopropylethylamine (DIEA, 1.6 mol, 280 mL). After a short wash procedure (1×DMF, 1×5% DIEA, 1×DCM; approximately 8 mL per packet), the tritylation procedure was repeated twice more by shaking overnight in a 0.05 M solution of trityl chloride in DCM (5.5 L) containing the same amount of base and washed (2×DMF, 1×5% DIEA, 3×DCM, 1×MeOH; approximately 8 mL per packet). The completeness of the trityl coupling was verified for each of the 46 different amino acid resins using the bromophenol blue color test (Krchnák, V., et al., Coll. Czech. Chem. Comm., 53:2542 (1988)).

3. Alkylation of the first amide position

All manipulations were performed under a nitrogen atmosphere and strictly anhydrous conditions. The 270 resin packets were dried overnight at 50 mTorr. Each of five groups, containing 46 amino acid resin packets plus control resin packets (including four Trt-Leu-MBHA packets and four Trt-Trp-MBHA packets), were placed in one of five separate round-bottom flasks—one for each of the five alkylation reactions. Each flask contained the same amount of available amide groups (11.07 mmol each). 1 M lithium t-butoxide in THF (220 mmol, 220 mL) and THF (220 mL) were added to each of the five reaction vessels and shaken at room temperature for 15 min. Excess base solution was removed by cannulation. Following addition of DMSO (440 mL), the individual alkylating agent was added (665 mmol i.e., 41.4 mL methyl iodide; 53.1 mL ethyl iodide; 57.5 mL allyl bromide; 79.0 mL benzyl bromide). 2-(Bromomethyl) naphthalene (665 mmol, 147 g) was dissolved in DMSO (440 mL) and transferred as a solution to the reaction vessel. The reaction mixture was vigorously shaken for 2 h at room temperature. The alkylation solution was removed by cannulation and the entire procedure repeated twice more. The resulting resin packets were washed (3×DMF, 2×IPA, 3×DCM, 1×MeOH; approximately 8 mL per packet) and dried. Following complete drying of the resin packets overnight at 50 mTorr, the process described above was repeated three times for allylation, benzylation and naphthylmethylation (each alkylation, 2×2 h and 1×5 h).

4. Recombine, mix and divide the resin

The resin of the 230 library packets was combined, mixed in DCM (2 L; 15 h shaking), and dried. The resin was divided into 250 polypropylene mesh packets (packet size 3 cm×3 cm; each containing 310 mg resin).

5. Removal of the trityl protecting group

The resin packets, prepared as described above, were washed (1×DCM; approximately 8 mL per packet), treated twice with 2% TFA in DCM (1×2 min, 1×30 min; 2 L), and washed (1×DCM, 2×IPA, 2×DCM, 1×MeOH; approximately 8 mL per packet).

6. Coupling of the second amino acid derivative and second alkylation

The amino acid coupling (using the 50 different amino acid derivatives), Fmoc removal, tritylation of the free amino groups, alkylation of the previously formed amide bond and trityl removal were performed as described above. Trt-Phe-Leu-NMe-MBHA resin packets and Trt-Ala-Trp (Me)-NMe-MBHA resin packets were added as control resins during alkylation. The second amide position was treated five times for alkylation (methylation and ethylation, each 5×2 h; allylation, benzylation and naphthylmethylation, each 3×2 h and 2×3 h).

7. HF cleavage

The 250 mixture resin packets were cleaved 24 at a time with hydrogen fluoride (5 mL per resin packet with 0.35 mL anisole added as scavenger) using a multiple vessel cleavage apparatus (Kornreich, W., et al., *Int. J. Pept. Protein Res.*, 25:414 (1985)). The resulting mixtures were extracted by sonicating with 50% aqueous acetonitrile (3×5 ml). The resulting solutions were lyophilized and relyophilized twice more from 50% aqueous acetonitrile.

8. Individual compounds

Individual compounds were prepared in the same manner as described for the library synthesis. The alkylations were generally performed with repetitions. Following HF cleavage, the crude individual compounds were purified by preparative RP-HPLC. Condition for preparative HPLC:vydac C18; linear gradient 25–55% B, in 30 min; eluent A:0.05% TFA aqueous;eluent B:0.05% TFA in acetonitrile; flow rate:20 mL/min; the eluent was monitored at 214 nm.

Phenylalanyl-N-methyl-leucinmethylamide. Yield after preparative HPLC (TFA salt): 59.8%. $^1$H NMR (200 MHz, CDCl$_3$; mixture of conformers; selected data for the major conformer; ratio 78:22): δ=0.85 (m; 6H), 1.23–1.57 (m; 2H), 1.71–1.85 (m; 1H), 2.65 (s; 3H), 2.7 (d; 3H), 3.01–3.28 (m; 2H), 4.51–4.58 (m; 2H), 6.85 (m; 1H), 7.15–7.28 (m; 5H), 8.5 (br; 2H). $^{13}$C NMR (200 MHz, CDCl$_3$; selected data for major conformer): δ=22.0, 22.7, 24.7, 26.1, 32.6, 36.8, 37.4, 51.7, 57.8, 128.1, 129.1, 129.4, 133.4, 168.9, 170.1. MALDI-MS: 307 (M+2), 329 (M+Na). Anal. calcd. for $C_{19}H_{28}F_3N_3O_4$ (TFA salt): C, 54.39; H, 6.73; N, 10.02. Found: C, 54.19; H, 7.03; N, 9.99. HR-FAB-MS calcd. for $C_{17}H_{28}N_3O_2$ (MH$^+$) 306.2175, found 306.2165.

Phenylalanyl-N-ethyl-leucinemethylamide. Yield after preparative HPLC (TFA salt): 18.8%. $^1$H NMR (200 MHz, CDCl$_3$; selected data for major conformer; ratio 72:28): δ=0.75–1.15 (m; 9H), 1.35–1.60 (m; 2H), 1.95–2.20 (m; 1H), 2.66 (d; 3H), 2.85–3.45 (m; 4H), 3.97 (m; 1H), 4.41 (m; 1H), 6.99 (m; 1H), 7.18–7.40 (m; 5H), 8.2–9.2 (br; 2H). $^{13}$C NMR (200 MHz, CDCl$_3$; selected data for major conformer): δ=14.3, 22.9, 23.1, 25.7, .26.6, 38.3, 43.5, 52.2, 58.3, 128.6, 129.6, 130.1, 134.1, 169.3, 171.2. MALDI-MS: 321 (M+1), 343 (M+Na). Anal. calcd. for $C_{20}H_{30}F_3N_3O_4$ (TFA salt) : C, 55.399; H, 6.9789; N, 9.697. Found: C, 54.39; H, 6.97; N, 9.47. HR-FAB-MS calcd. for $C_{18}H_{30}N_3O_2$ (MH$^+$) m/z=320.2331, found m/z=320.2335.

Phenylalanyl-N-allyl-leucinemethylamide. Yield after preparative HPLC (TPA salt): 20.05%. $^1$H NMR (200 MHz, CDCl$_3$; selected data for major conformer; ratio 71:29): δ=0.76–0.90 (m; 6H), 1.27–1.50 (m; 2H), 1.98–2.08 (m; 1H), 2.68 (d; 3H), 3.02–3.60 (m; 4H), 4.18 (m; 1H), 4.41–4.49 (m; 1H), 5.12–5.24 (m; 2H), 5.56–5.78 (m; 1H), 6.99 (m; 1H), 7.21–7.36 (m; aromatic protons), 8.35–9.35 (br; 2H). $^{13}$C NMR (200 MHz, CDCl$_3$; selected data for major conformer): δ=22.3, 25.0, 26.0, 37.8, 49.9, 51.8, 58.0, 119.9, 128.1, 129.1, 129.5, 132.1, 133.5, 169.1, 170.4. MALDI-MS: 333 (M+1), 355 (M+Na). Anal. calcd. for $C_{21}H_{30}F_3N_3O_4$ (TFA salt): C, 56.60; H, 6.79; N, 9.44. Found: C, 56.00; H, 6.83; N, 9.23. HR-FAB-MS calcd. for $C_{19}H_{30}N_3O_2$ (MH$^+$)m/z=332.2331, found m/z=332.2335.

Phenylalanyl-N-benzyl-leucinemethylamide. Yield after preparative HPLC (TFA salt): 20.34%. $^1$H NMR (200 MHz, CDCl$_3$; selected data for major conformer; ratio 65:35): δ=0.72–0.89 (m; 6H), 1.02–1.53 (m; 2H), 1.87–2.11 (m; 1H), 2.52 (d; 3H), 2.98–3.45 (m; 2H), 4.05–4.79 (m; 4H), 6.92 (m; 1H), 7.08–7.38 (m; 10H), 8.20–9.20 (br; 2H). $^{13}$C NMR (200 MHz, CDCl$_3$; selected data for major conformer): δ=22.0, 22.9, 25.5, 26.0, 37.7, 38.1, 47.3, 52.5, 57.9, 127.2, 127.7, 128.2, 129.3, 129.8, 133.5, 134.9, 169.7, 170.6. MALDI-MS: 383 (M+1), 405 (M+Na). Anal. calcd. for $C_{25}H_{32}F_3N_3O_4$ (TFA salt): C, 60.58; H, 6.512; N, 8.48. Found: C, 60.33; H, 6.41; N, 8.43. HR-FAB-MS calcd. for $C_{23}H_{32}N_3O_2$ (MH$^+$) m/z=382.2487, found m/z=382.2511.

Phenylalanyl-N-naphthylmethyl-leucinemethylamide. Yield after preparative HPLC (TFA salt): 18.54%. $^1$H NMR (200 MHz, CDCl$_3$ selected data for major conformer; ratio 67:33): δ=0.70–0.90 (m; 6H), 1.15–1.58 (m; 2H), 1.94–2.13 (m; 1H), 2.44 (d; 3H), 3.04–3.49 (m; 2H), 4.20–4.90 (m; 4H), 6.90–6.99 (m; 1H), 7.08–7.89 (m; 12H), 8.1–9.5 (br; 2H). $^{13}$C NMR (200 MHz, CDCl$_3$; selected data for major conformer): δ=22.0, 23.0, 25.5, 25.7, 37.7, 38.1, 52.6, 57.7, 124.6–134.2 (aromatic carbons), 169.8, 170.5. MALDI-MS: 433 (M+1), 455 (M+Na). Anal. calcd. for $C_{29}H_{34}F_3N_3O_4$ (TFA salt): C, 63.82; H, 6.28; N, 7.70. Found: C, 63.96; H, 6.27; N, 7.76. HR-FAB-MS calcd. for $C_{27}H_{34}N_3O_2$ (MH$^+$) m/z=432.2643, found m/z=432.2663.

EXAMPLE II

A. Synthesis of the resin bound peptidomimetic compound H$_2$N-Tyr(tBu)-N(Me)-Tyr(tBu)-N(Bzl)-resin 1. Coupling of the first amino acid derivative The peptidomimetic compound was synthesized using simultaneous multiple peptide synthesis (Merrifield, R. B. *J. Am. Chem. Soc.* 1963, 85, 2149; Houghten, R. A. *Proc. Natl. Acad. Sci. USA* 1985, 82, 5131) and Fmoc strategy. The solid support (MBHA resin) was contained in a polypropylene mesh packet (100 mg resin per packet; packet size 3 cm×3 cm).

After the neutralization and wash steps were carried out [1×DCM, 2×5% N,N-diisopropylethylamine (DIEA), 2×DCM, 2×DMF; approximately 5 mL for each washing step] the resin packet was vigorously shaken in a solution (5.4 mL) of 0.1 M Fmoc-L-Tyr(tBu)-OH (0.54 mmol)/DIC/ HOBt in DMF overnight. The resin packet was washed (2×DMF, 1×DCM, 1×MeOH) and the completeness of amino acid coupling was verified using the ninhydrin test (Kaiser, E. T.; Colescott, R. L.; Blossinger, C. D.; Cook, P. I. *Anal. Biochem.* 1970, 34, 595). One repetitive coupling was required. Removal of the Fmoc protecting group was accomplished by shaking the resin packet in 20% piperidine/ DMF (1×3 min, 1×10 min; 2 L) followed by a wash cycle (5×DMF, 2×IPA, 3×DCM).

2. Tritylation of the N-terminal amino group

The resin packet (0.09 mmol of free N-α-amino groups) was shaken for 2 h in a 0.077 M solution of trityl chloride (0.45 mmol) in DCM/DMF (9:1, 5.84 mL) containing DIEA (2.61 mmol, 0.45 mL). After a short wash procedure (1×DMF, 1×5% DIEA, 1×DCM), the tritylation procedure was repeated three more times by shaking overnight in a 0.077 M solution of trityl chloride in DCM (5.84 mL), for 3 h in a 0.077 M solution of trityl chloride in DCM/DMF (9:1, 5.84 mL) and again overnight in a 0.05 M solution of trityl chloride in DCM (9 mL), containing the same amount of base. The resin packet was washed (2×DMF, 1×5% DIEA, 3×DCM, 1×MeOH) and a small resin sample was tested for the completeness of the trityl coupling using the bromophenol blue color test (Krchňák, V.; Vágner, J.; Šafář, P.; Lebl, M. Coll. *Czech. Chem. Comm.* 1988, 53, 2542).

3. Alkylation of the first amide position

All manipulations were performed under a nitrogen atmosphere and strictly anhydrous conditions. The resin packet was dried overnight at 50 mTorr. 1 M lithium t-butoxide in THF (1.8 mmol, 1.8 mL) and THF (1.8 mL) were added to the reaction vessel containing the resin packet (0.09 mmol amide groups) and it was shaken at room temperature for 15 min. Excess base solution was removed by cannulation. Following addition of DMSO (3.6 mL), benzyl bromide (5.4 mmol, 0.64 mL) was added. The reaction mixture was vigorously shaken for 2 h at room temperature. The alkylation solution was removed by cannulation and the entire procedure repeated twice more. The resulting resin packet was washed (3×DMF, 2×IPA, 3×DCM, 1×MeOH; approximately 5 mL) and dried. Following complete drying of the resin packet overnight at 50 mTorr, the process described above was repeated again two times.

4. Removal of the trityl protecting group

The resin packet was washed (1×DCM; approximately 5 mL), treated twice with 2% TFA in DCM (1×3 min, 1×30 min), and washed (1×DCM, 2×IPA, 2×DCM, 1×MeOH; approximately 5 mL).

5. Coupling of the second amino acid derivative and second alkylation

The coupling of Fmoc-L-Tyr(tBu)-OH to the resin bound compound, the Fmoc removal, and the tritylation (only three treatments were required) of the free amino groups were performed as described above.

6. Alkylation of the second amide position

All manipulations and the base treatment were performed as described above. For the alkylation DMSO (3.6 mL) and methyl iodide (5.4 mmol, 0.34 mL) were added. The reaction mixture was vigorously shaken for 2 h at room temperature. The alkylation solution was removed by cannulation and the entire procedure repeated twice more. The resulting resin packet was washed (3×DMF, 2×IPA, 3×DCM, 1×MeOH; approximately 5 mL) and the trityl protecting group removed as described above.

B. Synthesis of $(CH_3)_2CH$—NH-Tyr(tBu)-N(Me)-Tyr(tBu)-N(Bzl)-resin

1. Reductive alkylation

This procedure was adapted from those known in the art: Borch, R. F., et al., *J. Am. Chem. Soc.*, 93:2897 (1971); Coy, D. H., et al., *Tetrahedron*, 44:835 (1988); Staňková, M., et al., *Drug Development Research*, 33:146 (1994)(herein incorporated by reference).

Resin packets containing resin bound compounds with free N-terminal amino groups were shaken in a solution of methanol (MeOH) 20%/dichloromethane (DCM) 79%/ acetic acid 1% (for one resin packet containing 0.05 mmol amine 4 ml of solvent were used—enugh to cover the resin packet) and 2–10 equivalents of the aldehyde or ketone (depending on their reactivity). After 20 minutes, 2–10 equivalents of a 1 M solution of sodium cyanoborohydride in N,N-dimethylformamide (DMF) were added and the reaction mixture shaken for 60 min. The resin packets were washed using the following washing sequence: 5×DMF, 1×DCM, 1×MeOH (for one resin packet of the size mentioned above approximately 5 ml of solvent for each step). The completeness of the formation of secondary amines can be tested using hte Kaiser test. If necessary the reaction can be repeated, also by using a different solvent system like DMF containing 1% acetic acid.

The applicability of this reaction to all amino acid derivatives used in the peptidomimetic library was applied to sets of 50 model dipeptide resins (OL-resins). Following HF cleavage, the model compounds were analyzed by HPLC and MALDI-MS. This procedure was carried out as described in R. F. Borch, et al., *J. Am. Chem. Soc.*, 93:2897–2904 (1971); D. H. Coy, et al., *Tetrahedron*, 44:835–841(1988); and M. Stankova, et al., *Drug Development Research*, 33:146–156 (1994)(all of which are herein incorporated by reference).

Following neutralization (3×5% DIEA, 2×DCM) and a washing step (1×DMF/2% acetic acid), the resin packet was shaken in a solution of MeOH 20%/DCM 79%/acetic acid 1% (4 mL) and acetone (0.9 mmol; 66.6 μL). After 20 min 0.9 mL (0.9 mmol) of a 1 M solution of sodium cyanoborohydride in DMF were added and the reaction mixture was shaken for 60 min. The resin packet was washed using the following washing sequence: 5×DMF, 1×DCM, 1×MeOH, approximately 5 ml of solvent for each step. The completeness of the formation of the secondary amines was tested using the Kaiser test [if necessary the reaction can be repeated, also by using a different solvent system like DMF containing 1% acetic acid].

C. Synthesis of red[$(CH_3)_2CH$—NH-Tyr(tBu)-N(Me)-Tyr(tBu)-NH(Bzl)]; (red=reduced)

1. Reduction

Reduction can either be performed on solid support [procedure A] or in solution [procedure B].

Procedure A:

Into a 50 ml glass tube (teflon-lined cap) were added the resin packet and 310 mg boric acid (5.014 mmol). Under nitrogen atmosphere, 0.5 ml trimethylborate (0.0042 mmol) were added, followed by the addition of 15 ml of 1 M borane-tetrahydrofuran complex (15 mmol). Following cessation of hydrogen evolution, the tube was sealed and heated at 65° C. for 100 hr. The tubes were then removed, cooled to room temperature and 2 ml methanol were added to quench excess reducing agent. The resin packet was washed with THF (1×1 min×10 ml) and MeOH (4×1 min×10 ml). After drying the resin packet, it was covered with 15 ml piperidine and heated at 65° C. for 18 hr. The resin packet was washed with DMF (2×1 min×5 ml), DCM (2×1 min×5 ml), MeOH (1×1 min×5 ml), DMF (2×1 min×5 ml), DCM (2×1 min×5 ml) and MeOH (1×1 min×5 ml).

Procedure B:

The following procedure was adapted from Dooley, C. T., et al., *Analgesia, INRC Proceedings,* 1:400 (1995)(herein incorporated by reference). Into a 50 ml glass tube (teflon-lined cap) were added the compound (0.09 mmol; two backbone carbonyl groups) and 310 mg boric acid (5.014 mmol). Under nitrogen atmosphere, 0.5 ml trimethylborate (0.0042 mmol) were added, followed by the addition of 15 ml of 1 M borane-tetrahydrofuran complex (15 mmol). Following cessation of hydrogen evolution, the tube was sealed and heated at 60° C. for 90 hr. The tubes were cooled to room temperature and 5 ml methanol were added dropwise to remove excess reducing agent. Excess solvent was removed by immersion of the tube in a 55° C. water bath under a constant nitrogen flow (10–15 psi). The compound subsequently underwent successive washes and evaporations with methanol (2×5 ml). After addition of 2 N hydrogen chloride (3 mL; 6 mmol) in water/MeOH (1:3) the glass tube was sealed and heated at 60° C. for 18 h to hydrolyze boron-nitrogen complexes. The tube was removed from heat, MeOH (2 ml) was added and the solvent evaporated.

C. HF cleavage—Soluble Compounds

The compound was cleaved from the resin with hydrogen fluoride (5 mL per resin packet with 0.35 mL anisole added as scavenger) using a multiple vessel cleavage apparatus (Houghten, R. A., et al., *Int. J. Pept. Protein Res.,* 27:673 (1986)). If the compound has been reduced on the solid support, the cleavage time was 9 h at 0° C.; the nonreduced compound was cleaved in 90 min at 0° C. The resulting compound was extracted by sonicating with 50% aqueous acetonitrile (3×5 ml). The resulting solution was lyophilized and relyophilized twice more from 50% aqueous acetonitrile.

EXAMPLE III

A. Identification Of Mu Selective Opioid Peptides By A Radioreceptor Assay

This example describes the identification of individual compounds, either contained within a synthetic combinatorial library mixture or prepared separately, as inhibitors of the μ-selective opioid peptide [$^3$H]-[D-Ala$^2$, MePhe$^4$, Gly-Ol$^5$ enkephalin ([$^3$H]-DAMGO). Individual peptides were identified as capable of inhibiting [$^3$H]-DAMGO by a radioreceptor assay.

As detailed below, the compound libraries of the instant invention were screened at a single concentration (0.08 mg/ml) in a radioreceptor assay using rat brain homogenates and [$^3$H]-DAMGO as radioligand. IC$_{50}$ values were determined for mixtures in the library which significantly inhibited the binding of [$^3$H]-DAMGO.

B. Radioreceptor Assays Selective For The Mu Receptor

Rat and guinea pig brains, frozen in liquid nitrogen, were obtained from Harlan Bioproducts for Science (Indianapolis, Ind.). Frozen brains were thawed, the cerebella removed and the remaining tissue weighed. Each brain was individually homogenized in 40 ml Tris-HCl buffer (50 mM, pH 7.4, 4° C.) and centrifuged (39000×g) (Model J2-HC; Beckman Instruments, Fullerton, Calif.) for 10 min at 4° C. The pellets were resuspended in fresh Tris-HCl buffer and incubated at 37° C. for 40 min. Following incubation, the suspensions were centrifuged as above, the resulting pellets resuspended in 100 volumes of Tris buffer and the suspensions combined. Membrane suspensions were prepared and used in the same day. Protein content of the crude homogenates ranged from 0.15–0.2 mg/ml as determined using the method described by Bradford (Bradford, *Anal. Biochem.* 72:248–254 (1976), which is incorporated herein by reference).

Binding assays were carried out in polypropylene tubes. Each tube contained 0.5 ml of membrane suspension, 3 nM of the μ-selective opioid peptide [$^3$H]-DAMGO (specific activity 36 Ci/mmol), 0.08 mg/ml compound mixture and Tris-HCl buffer in a total volume of 0.65 ml. Assay tubes were incubated for 60 min at 25° C. The reaction was terminated by filtration through GF-B filters (Wallac, Inc., Gaithersburg, Md.). The filters were subsequently washed with 6 ml Tris-HCl buffer at 4° C. Bound radioactivity was counted on a Beta-plate Liquid Scintillation Counter (Life Technologies, Gaithersburg, Md.) and expressed in counts per minute (cpm). Inter- and intra-assay variation standard curves were determined by incubation of [$^3$H]-DAMGO in the presence of 0.13–3900 nM of unlabeled DAMGO. Competitive inhibition assays were performed as above using serial dilutions of the peptide mixtures. IC$_{50}$ values were then calculated using the software GRAPHPAD (ISI, San Diego, Calif.). IC$_{50}$ values of less than 1000 nM are indicative of highly active opioid compounds which bind to the μ receptor, with particularly active compounds having IC$_{50}$ values of 100 nM or less and the most active compounds with values of less than 10 nM.

In the following Table, the only variable occurs at R$_7$. Thus, all of the following compounds, in reference to Formula I, have the following structure: X and Y are taken together to form a carbonyl group, R$_1$ and R$_2$ are each a hydrogen atom, R$_{10}$ is absent, B is zero, AA, BB, and CC are zero, R$_6$ is ethyl, R$_8$ is napth-2-ylmethyl, and R$_9$ is a hydrogen atom.

TABLE 1

Mu Receptor Assay

| R$_7$ | IC$_{50}$ (nM) |
|---|---|
| S-methyl | 2 |
| S-(2-(methylsulfinyl)ethyl) | 7 |
| hydrogen atom | 13 |
| S-(4-hydroxy)benzyl (2-BrZ)[1] | 31 |
| S-(Hydroxy)methyl | 40 |
| S-(4-hydroxybenzyl) (t-butyl)[1] | 74 |
| S-(indol-3-yl)methyl (Boc)[1] | 92 |
| S-(1-methyl)prop-1-yl | 129 |
| S-(3-(N,N,N-triethyl)guanidino)-N-propyl) | 138 |
| S-(4-(N-(naphth-2-ylmethyl)amino)-n-butyl | 237 |
| R-methyl | 246 |
| S-Cyclohexylmethyl | 265 |
| S-Phenyl | 384 |
| S-Benzyl | 471 |
| R-(4-(N-(naphth-2-ylmethyl)amino)-n-butyl) | 476 |
| S-(2-carboxy)eth-1-yl | 476 |
| S-(N-(napth-2-ylmethyl)indol-3-ylmethyl) | 494 |
| R-4-(hydroxy)benzyl | 542 |
| S-(N,N-di(napth-2-ylmethyl)amidoethyl | 585 |
| R-(2-methyl)prop-1-yl | 666 |
| S-Pyrrolidine (taken in conjunction with R$_8$) | 891 |
| R-(n-butyl) | 1056 |
| S-((N,N-di(naphth-2-ylmethyl)amidomethyl)) | 1106 |
| R-(Hydroxy)methyl | 1106 |
| R-Pyrrolidine (takin in conjunction with R$_8$) | 1115 |
| S-(n-propyl) | 1133 |
| S-(Napth-2-yl)methyl | 1206 |
| R-(n-propyl) | 1343 |
| S-(2-methyl)prop-1-yl | 1493 |
| S-(n-butyl) | 1560 |
| R-(indol-3-yl)methyl (Boc)[1] | 1593 |
| R-(3-(N,N,N-triethyl)guanidino)-N-propyl) | 1630 |

[1]Protecting group removed before testing

EXAMPLE IV

A. Assay for Kappa Opiate Receptor Inhibition

This example demonstrates the specificity of the novel selectively N-alkylated compounds of Formula I for the kappa opiate receptors.

Assays demonstrating selective inhibition of binding to kappa oppiate receptors for K receptors were carried out using [$^3$H]-U69,593 (3 nM, specific activity 62 Ci/mmol) as the radioligand and tissue homogenates prepared from guinea pig brains (cortex and cerebellum) using Tris buffer containing 100 μM PMSF, 5 mM MgCl$_2$ and 1 mg/ml BSA, pH 7.4. Sample tubes were incubated for 2.5 hr. Standard curves were prepared using 0.05–6300 nM naloxone.

Tritiated ligands, [$^3$H]-DAMGO, [$^3$H]-DPDPE and [$^3$H]-[D-Ser$^2$, Leu$^5$, Thr$^6$]enkephalin ([$^3$H]-DSLET), Abuse (NIDA) repository, as prepared by Multiple Peptide Systems (San Diego, Calif.), [$^3$H]-U69,593 from Amersham (Arlington Heights, Ill.) and [$^3$H]-naltrindole from DuPont NEN Research Products (Los Angeles, Calif.). The average standard deviation for IC$_{50}$ values was ±20%.

In the following Table 2, all compounds have either R$_1$ or R$_2$ as a hydrogen atom and the other taken together with R$_3$ to form a pyrrolidine group. X and Y are taken together to form a carbonyl group, B is zero, AA, BB, and CC are zero except where noted, R$_6$ is benzyl and R$_9$ is a hydrogen atom. Thus, only R$_7$ is varied as the compounds are tested in the assay.

TABLE 2

Kappa Receptor Assay

| R$_7$ | IC$_{50}$ (nM) |
|---|---|
| S-methyl | 1 |
| R-methyl | 1 |
| hydrogen atom | 1 |
| S-(3-guanidino)-N-propyl) | 2 |
| S-(4-(N-benzylamino)-n-butyl | 4 |
| S-(iso-propyl) | 7 |
| S-(2-(methylsulfinyl)ethyl) | 11 |
| S-(n-propyl) | 14 |
| R-(n-propyl) | 15 |
| R-(hydroxy)methyl | 16 |
| R-(n-butyl) | 21 |
| R-(3-guanidino)-N-propyl | 22 |
| R-(Naphth-2-yl)methyl | 23 |
| S-(hydroxy)methyl | 28 |
| R-(n-butyl) | 31 |
| R-(4-(N-benzylamino)-n-butyl | 42 |
| S-Phenyl | 50 |
| S-Benzyl | 53 |
| S-(4-hydroxybenzyl) | 56 |
| R-(1-methyl)propyl | 67 |
| R-(4-hydroxybenzyl) (t-butyl)[1] | 69 |
| S-(1-methyl)propyl | 74 |
| S-(4-hydroxybenzyl) (t-butyl)[1] | 85 |
| S-(2-methyl)propyl | 99 |
| S-(Cyclohexylmethyl) | 102 |
| S-(1-hydroxy)ethyl | 108 |
| R-benzyl | 146 |
| R-(iso-propyl) | 203 |
| S-(Naphth-2-ylmethyl) | 222 |
| R-pyrrolidine (taken in conjunction with R$_8$) | 247 |
| R-Cyclohexylmethyl | 284 |
| R-(2-methyl)propyl | 291 |
| S-(indol-3-yl)methyl (Boc)[1] | 306 |
| S-(N,N-dibenzylamido)ethyl | 313 |
| hydrogen atom (AA = 1) | 487 |
| R-(N'(t-butoxycarbonyl)indol-3-ylmethyl) | 496 |
| R-(propionamide) | 642 |
| 1-(hydroxy)ethyl | 650 |
| 2-(carboxy)ethyl | 898 |

TABLE 2-continued

Kappa Receptor Assay

| R$_7$ | IC$_{50}$ (nM) |
|---|---|
| R-(indol-3-ylmethyl) | 931 |
| S-(indol-3-ylmethyl) | 1277 |
| R-(N,N-dibenzylamido)methyl | 2430 |
| R-(2-(carboxy)ethyl) | 4688 |
| S-(4-hydroxy-pyrrolidine) taken in conjunction with R$_8$ | 8735 |
| S-pyrrolidine (taken in conjunction with R$_8$) | 13533 |

[1]Protecting group removed before testing

EXAMPLE V

A. α-Glucosidase Inhibitor

α-Glucosidases are not only essential to carbohydrate metabolism, but also vital for the processing of various glycoproteins and glycolipids. Inhibitors of these enzymes, in particular of α-glucosidase, are therefore of high therapeutic potential. α-glucosidase inhibitors are potent oral anti-diabetics (Lebovitz, H. E. *Drugs,* 44(3):21–28 (1992)), and have been implicated in the blocking of microbial infection (Fischer, P. B., et al. *J.Virol.* 69(9):5791–5797 (1995); Rademacher, T. W., IN: Sandler, M. and Smith, J. H. (Eds.), Enzymes as Drugs Vol.2, Oxford University Press, Oxford, 333–343 (1994)) and tumor growth (Pili, R. et al., *Cancer Res.,* 55:2920–2926 (1995)). Most of the known natural and synthetic α-glucosidase inhibitors are sugar analogs, such as pseudooligosaccharides (Bischoff, H., *Eur.J.Clin.Investig.,* 24(3):3–10 (1994)), azasugars (Wong, C. H., et al., *J.Org.Chem.,* 60:1492–1501 (1995)), or indolizidine alkaloids (Elbein, A. D., *Ann.Rev.Biochem.,* 56:497–534 (1987)). Glycosidase inhibitors often inhibit more than one glycolytic enzyme (Kajimoto, T., et al., *J.Am.Chem.Soc.,* 113:6187–6196 (1990)).

The results set forth below in Table 3 are obtained from an α-glucosidase inhibition assay performed in a 96-well format using p-nitrophenyl-α-D-glucopyranoside as chromogenic substrate and α-glucosidase from bakers yeast, essentially as described by Haslvorson and Ellias (*Biochem. Biophys. Acta,* 30:28–40 (1958)). The IC$_{50}$ values represent the concentration necessary for 50% enzyme inhibition. The most active inhibitors are compounds of Formula I wherein X and Y are taken together to form a carbonyl group, B is zero, AA, BB, and CC are zero except were noted, R$_9$ is a hydrogen atom, R$_8$ is benzyl, R$_6$ is naphth-2-ylmethyl, R$_3$ is S-(N-(naphth-2-ylmethyl)indol-3-ylmethyl), R$_1$ and R$_2$ are each hydrogen, R$_{10}$ is absent, and R$_7$ is as set forth in the following Table 3:

TABLE 3

α-Glucosidase Inhibition Assay

| R$_7$ | IC$_{50}$ (μM) |
|---|---|
| R-(4-(N-benzylamino)-n-butyl) | 17 |
| S-(4-(N-benzylamino)-n-butyl) | 19 |
| S-(3-guanidino)-n-propyl) | 38 |
| R-(3-guanidino)-n-propyl) | 38 |
| S-pyrrolidine (taken in conjunction with R$_8$) | 141 |
| S-methyl | 167 |
| Hydrogen atom | 167 |

TABLE 3-continued

α-Glucosidase Inhibition Assay

| $R_7$ | $IC_{50}$ ($\mu$M) |
|---|---|
| R-(2-methyl)propyl | 170 |
| S-(1-hydroxymethyl) | 176 |
| S-(phenyl) | 184 |
| S-(4-hydroxybenzyl) | 190 |
| R-methyl | 199 |
| S-benzyl | 328 |
| S-(2-methyl)propyl | 356 |
| S-(indol-3-ylmethyl) | 356 |
| S-(iso-propyl) | 356 |
| R-(2-methyl)prop-1-yl | 398 |
| S-4-hydroxyprrolidine (in conjunction with $R_8$) | 437 |
| S-(1-hydroxyethyl) | 460 |
| S-[N',N'-dibenzylamido)ethyl]) | 529 |
| R-(4-hydroxybenzyl) | 540 |
| R-(iso-propyl) | 552 |
| R-(N'-benzyl indol-3-ylmethyl) | 552 |
| S-(2-(methylsulfinyl)ethyl) | 564 |
| S-(1-methyl)prop-1-yl | 610 |
| S-(N'-benzyl indol-3-ylmethyl) | 632 |
| S-(n-propyl) | 632 |
| R-(indol-3-ylmethyl) | 667 |
| S-(cyclohexylmethyl) | 667 |
| R'-(1-hydroxyethyl) | 678 |
| R-pyrrolidine (taken in conjunction with $R_8$) | 702 |
| S-[N',N'-dibenzylamido)ethyl | 713 |
| R-(n-butyl) | 724 |
| hydrogen atom, AA = 1 | 770 |
| R-(n-propyl) | 828 |
| S-(n-butyl) | >1000 |
| S-(napth-2-ylmethyl) | >1000 |
| R-(napth-2-ylmethyl) | >1000 |
| R-(1-hydroxyethyl) | >1000 |
| S-(2-carboxyethyl) | >1000 |
| R-(2-carboxyethyl) | >1000 |
| N',N-dibenzyl R-propionamide | >1000 |
| R-(cyclohexylmethyl) | >1000 |
| R-benzyl | >1000 |
| S-[(N'N'-dibenzylamido)ethyl | >1000 |

Numerous modifications and variations are possible in light of the above teachings and, therefore, within the scope of the appended claims, the invention may be practiced otherwise than as particulary described above.

We claim:

1. A single compound of the Formula (I):

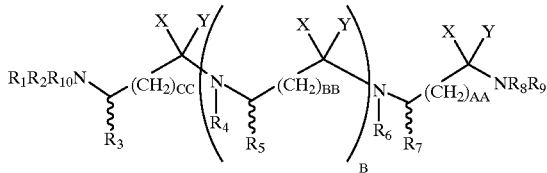

wherein:

$R_1$ and $R_2$ independently are a hydrogen atom, an amino protecting group, $C_1$ to $C_{12}$ acyl, $C_3$ to $C_{10}$ cycloalkyl, $C_3$ to $C_6$ heterocycle, $C_1$ to $C_{12}$ alkyl, $C_1$ to $C_{12}$ substituted alkyl, $C_7$ to $C_{16}$ alkylaryl, $C_7$ to $C_{16}$ substitued alkylaryl, a $C_6$ to $C_{15}$ alkyl heterocycle, or a substituted $C_6$ to $C_{15}$ alkyl heterocycle;

$R_3$, $R_5$, and $R_7$ are independently a hydrogen atom, $C_1$ to $C_{12}$ alkyl, $C_1$ to $C_{12}$ substituted alkyl, phenyl, substituted phenyl, $C_7$ to $C_{16}$ alkylaryl, $C_7$ to $C_{16}$ substituted alkylaryl, a $C_6$ to $C_{15}$ alkyl heterocycle, or a substituted $C_6$ to $C_{15}$ alkyl heterocycle;

$R_4$, $R_6$, and $R_8$ are independently a $C_1$ to $C_{18}$ substituent group; with the proviso that all but one of $R_4$, $R_6$ and $R_8$ can simultaneously be the same group;

$R_9$ is a hydrogen atom or a solid support;

$R_{10}$ is optionally present as a $C_1$ to $C_{18}$ substituent group when $R_1$ and $R_2$ are other than a hydrogen atom or an amino protecting group;

AA, BB, and CC are independently 0 to 5;

B is from 0 to 3;

further wherein the stereochemistry at the carbons bonded to $R_3$, $R_5$, and $R_7$ are independently R or S or a mixture of the two;

further wherein, when B is 2 or 3, each $R_4$ and $R_5$ can be the same or different;

further wherein, when B is 0, each $R_6$ and $R_8$ is different;

with the proviso that either $R_1$ or $R_2$ can be taken with $R_3$; $R_4$ can be taken with $R_5$; $R_6$ can be taken with $R_7$; respectively and independently, to form a subtituted or unsubstituted pyrrolidine ring;

X and Y are either 1) each a hydrogen atom or 2) taken together to represent a carbonyl group;

and a pharmaceutically acceptable salt, solvate or hydrate thereof.

2. The single compound of claim 1, wherein X and Y are taken together to form a carbonyl moiety.

3. The single compound of claim 2, wherein B, AA, BB and CC are zero, except that AA can be zero or one when $R_7$ is a hydrogen atom and that CC can be zero or one when $R_3$ is a hydrogen atom.

4. The single compound of claim 3, wherein $R_9$ is a hydrogen atom and $R_{10}$ is absent.

5. The single compound of claim 4, wherein $R_3$ and $R_7$ are independently chosen from the group consisting of S- or R-methyl, S- or R-benzyl, a hydrogen atom, S- or R-(but-2-yl), S- or R-(4-(N-methylamino)-n-butyl), S- or R-(4-(N-ethylamino)-n-butyl), S- or R-(4-(N-allylamino)-n-butyl), S- or R-(4-(N-benzylamino)-n-butyl), S- or R-(4-(N-(napth-2-ylmethylamino)-n-butyl), S- or R-(4-(amino)-n-butyl), S- or R-(sec-butyl), S- or R-(methylsulfinyl)eth-1-yl, S- or R-acetamido, S- or R-(2-(N,N-dimethyl)acetamido), S- or R-(N,N-diethyl)acetamido, S- or R-(N,N-diallyl)acetamido, S- or R-(n-allyl)acetamido, S- or R-(N,N-dibenzyl) acetamido, S- or R-(N-benzyl)acetamido, S- or R-(N,N-di (napth-2-ylmethyl))acetamido, S- or R-(N-(napth-2-ylmethyl))acetamido, S- or R-n-propylamine, S- or R-propionamido, S- or R-(N,N-dimethyl)propionamido, S- or R-(N,N-diethyl)propionamido, S- or R-(N,N-diallyl) propionamido, S- or R-(N,N-dibenzyl)propionamido, S- or R-(N,N-di(napth-2-ylmethyl)propionamido, S- or R-(3-(guanidino)-n-propyl), S- or R-((N,N-diallyl)-3-guanidino-n-propyl), S- or R-((N,N,N'-triallyl)-3-guanidino-n-propyl), S- or R-((N,N,N'-trimethyl)-3-(guanidino)-n-propyl), S- or R-((N,N,N'-triethyl)-3-(guanidino)-n-propyl), S- or R-hydroxymethyl, S- or R-(1-(hydroxy)ethyl), S-phenyl, S- or R-(2-(carboxy)ethyl), S- or R-(iso-propyl), S- or R-((indol-3-yl)methyl), S- or R-((N-(methyl)indol-3-yl) methyl), S- or R-((N-(ethyl)indol-3-yl)methyl), S- or R-((N-(allyl)indol-3-yl)methyl), S- or R-((N-(benzyl)indol-3-yl) methyl), S- or R-((N-(naphth-2-ylmethyl)indol-3-yl) methyl), S- or R-(4-((methoxy))benzyl, S- or R-(4-(ethoxy)) benzyl, S- or R-(4-(allyloxy))benzyl, S- or R-(4-hydroxybenzyl), S- or R-(n-butyl), S- or R-(n-propyl), S- or R-((napth-2-yl)methyl), AA is zero or one when $R_7$ is a hydrogen atom, CC is zero or one when $R_3$ is a hydrogen atom, S- or R-(cyclohexylmethyl), S- or R-(thiomethyl), or when either $R_1$ or $R_2$ are taken together with $R_3$ to form an S- or R-pyrrolidine or S-(4-(hydroxy)pyrrolidine).

6. The single compound of claim 5, wherein $R_6$ and $R_8$ are independently methyl, ethyl, allyl, benzyl, or napth-2-ylmethyl.

7. The single compound of claim 6, wherein either $R_1$ $R_2$ are each a hydrogen atom, or one of $R_1$ or $R_2$ is a hydrogen atom and the other is taken together with $R_3$ to form an S-pyrrolidine ring.

8. The single compound of claim 7, wherein one of $R_1$ or $R_2$ is a hydrogen atom and the other is taken together with $R_3$ to form an S-pyrrolidine ring.

9. The single compound of claim 8, wherein $R_6$ is napth-2-ylmethyl and $R_8$ is benzyl.

10. The single compound of claim 9, wherein $R_7$ is S- or R-methyl, a hydrogen atom, S- or R-(3-(guanidino)-n-propyl), S- or R-(4-(N-benzylamino)-n-butyl), S-(iso-propyl), S-(2-(methylsulfinyl)ethyl), S- or R-(n-propyl), S- or R-(hydroxymethyl), S- or R-(n-butyl), R-((napth-2-yl)methyl), or S-phenyl.

11. The single compound of claim 10, wherein $R_7$ is S- or R-methyl.

12. The single compound of claim 7, wherein $R_1$ and $R_2$ are each a hydrogen atom and $R_3$ is S-benzyl.

13. The single compound of claim 12, wherein $R_6$ is ethyl and $R_8$ is (napth-2-yl)methyl.

14. The single compound of claim 13, wherein $R_7$ is S-methyl, S-(2-(methylsulfinyl)ethyl), a hydrogen atom, S-(4-(hydroxy)benzyl) or S-((hydroxy)methyl).

15. The single compound of claim 14, wherein $R_7$ is S-methyl.

16. The single compound of claim 7, wherein $R_1$ and $R_2$ are each a hydrogen atom and $R_3$ is R-((N-(napth-2-ylmethyl)indol-3-yl)methyl).

17. The single compound of claim 16, wherein $R_6$ is napth-2-ylmethyl and $R_8$ is benzyl.

18. The single compound of claim 17, wherein $R_7$ is S- or R-(3-(guanidino)-n-propyl) or S- or R-(4-(benzylamino)-n-butyl).

19. The single compound of claim 6, wherein either $R_1$ or $R_2$ is a hydrogen atom or is taken in conjunction with $R_3$ to form a pyrrolidine ring, and the other is $C_1$ to $C_{12}$ acyl, $C_3$ to $C_{10}$ cycloalkyl, $C_3$ to $C_6$ heterocycle, $C_1$ to $C_{12}$ alkyl, $C_1$ to $C_{12}$ substituted alkyl, $C_7$ to $C_{16}$ alkylaryl, $C_7$ to $C_{16}$ substituted alkylaryl, a $C_6$ to $C_{15}$ alkyl heterocycle, or a substituted $C_6$ to $C_{15}$ alkyl heterocycle.

20. The single compound of claim 1, wherein X and Y are each a hydrogen atom.

21. The single compound of claim 20, wherein B, AA, BB and CC are zero, except that AA can be zero or one when $R_7$ is a hydrogen atom and that CC can, be zero or one when $R_3$ is a hydrogen atom.

22. The single compound of claim 21, wherein $R_9$ is a hydrogen atom and $R_{10}$ is absent.

23. The single compound of claim 22, wherein $R_6$ and $R_8$ are independently methyl, benzyl or 4-hydroxybenzyl.

24. The single compound of claim 23, wherein $R_3$ and $R_7$ are independently S-benzyl or S-(4-hydroxybenzyl).

25. The single compound of claim 24, wherein $R_8$ is benzyl, $R_7$ is 4-hydroxybenzyl, $R_6$ is methyl, $R_3$ is 4-hydroxybenzyl.

26. The single compound of claim 25, wherein a)$R_1$ and $R_2$ are the same and are methyl or a hydrogen atom; b)either $R_1$ or $R_2$ is a hydrogen atom and the other is chosen from the group consisting of methyl, iso-propyl, cyclopropylmethyl, 4-hydroxymethyl, N-methylpiperidin-4-yl, and 3-(N,N-dimethylamino)-2-methyl-prop-2-en-1-yl.

27. The single compound of claim 24, wherein $R_8$ is methyl, $R_7$ is S-benzyl, $R_6$ is 4-hydroxybenzyl, and $R_3$ is S-(4-hydroxybenzyl).

28. The single compound of claim 27, wherein $R_1$ and $R_2$ are the same and are either a hydrogen atom or methyl, or one of $R_1$ or $R_2$ is a hydrogen atom and the other is methyl.

29. The single compound of claim 24, wherein $R_8$ is methyl, $R_7$ is S-(4-hydroxymethyl), $R_6$ is benzyl, and $R_3$ is S-(4-hydroxybenzyl).

30. The single compound of claim 29, wherein $R_1$ and $R_2$ are the same and are either a hydrogen atom or methyl, or one of $R_1$ or $R_2$ is a hydrogen atom and the other is methyl.

* * * * *